US008738127B1

(12) United States Patent
Lebovitz et al.

(10) Patent No.: US 8,738,127 B1
(45) Date of Patent: May 27, 2014

(54) METHOD OF TREATING A PATIENT

(75) Inventors: Harold Lebovitz, Staten Island, NY (US); Paul Goode, Cherry Hills, NJ (US); Walid Haddad, Haifa (IL); Shlomo Ben-Haim, Orangeburg, NY (US); Irit Yaniv, Ramat-Gan (IL); Benny Rousso, Rishon-LeZion (IL)

(73) Assignee: MetaCure Limited, Hamilton (BM)

(*) Notice: Subject to any disclaimer, the term of this patent is extended or adjusted under 35 U.S.C. 154(b) by 0 days.

(21) Appl. No.: 13/450,798

(22) Filed: Apr. 19, 2012

Related U.S. Application Data

(60) Provisional application No. 61/477,194, filed on Apr. 20, 2011.

(51) Int. Cl.
*A61N 1/00* (2006.01)

(52) U.S. Cl.
USPC .................................................. 607/3

(58) Field of Classification Search
USPC .................................................. 607/3, 44
See application file for complete search history.

(56) References Cited

U.S. PATENT DOCUMENTS

| | | | |
|---|---|---|---|
| 6,571,127 B1 | 5/2003 | Ben-Haim et al. | |
| 7,512,442 B2 | 3/2009 | Flesler et al. | |
| 7,840,269 B2 | 11/2010 | Policker et al. | |
| 2009/0281449 A1 | 11/2009 | Thrower et al. | |
| 2011/0238128 A1* | 9/2011 | Dobak, III | 607/44 |

FOREIGN PATENT DOCUMENTS

WO WO 2011/092710 8/2011

OTHER PUBLICATIONS

Lam et al. "Hypothalamic Sensing of Circulating Fatty Acids is Required for Glucose Homeostasis", Nature Medicine, 3: 320-327, 2005.

Leitão et al. "Lipotoxicity and Decreased Islet Graft Survival", Diabetes Care, 33(3): 658-660, Mar. 2010.

Lebovitz et al. "Fasting Plasma Triglycerides Predict the Glycaemic Response to Treatment of Type 2 Diabetes by Gastric Electrical Stimulation. A Novel Lipotoxocity Paradigm", Diabetic Medicine, 30(6): 687-693, Jun. 2013.

Sanmiguel et al. "Gastric Electrical Stimulation With the TANTALUS® System in Obese Type 2 Diabetes Patients: Effect on Weight and Glycemic Control", Journal of Diabetes Science and Technology, 3(4): 964-970, Jul. 2009.

Lebovitz et al. "21-LB Existance of A Triglyceride-Dependent Glycemic Regulatory Pathway in Patients With Type 2 Diabetes", Poster Presented at the Annual Scientific Meeting of the American Diabetes Association, Chicago, Ill., USA, Jun. 23, 2013.

* cited by examiner

*Primary Examiner* — Robert N Wieland

(57) ABSTRACT

There is provided in accordance with an exemplary embodiment of the invention a method of treating diabetic patients comprising measuring a triglyceride level in a diabetic patient and applying a diabetes treatment according to the triglyceride level. Optionally, there is provided a method of screening. Alternatively or additionally, there is provided a method of weight loss. Alternatively or additionally, there is provided a method of relatively reducing HOMA-IR levels. Alternatively or additionally, there is provided a method of relatively reducing blood pressure. An exemplary device to apply the treatment is described.

43 Claims, 12 Drawing Sheets

108
102
110
102
102
104
100
Memory 112
106

METHOD OF TREATING A PATIENT

RELATED APPLICATION

This application claims the benefit of priority under 35 USC §119(e) of U.S. Provisional Patent Application No. 61/477,194 filed Apr. 20, 2011, the contents of which are incorporated herein by reference in their entirety.

FIELD AND BACKGROUND OF THE INVENTION

The present invention, in some embodiments thereof, relates to a method of treating patients and, more particularly, but not exclusively, to a method of treating patients according to triglyceride levels.

Flesler et al. in U.S. Pat. No. 7,512,442 disclose:

"Apparatus is provided for treating a condition such as obesity. The apparatus includes a set of one or more electrodes, which are adapted to be applied to one or more respective sites in a vicinity of a body of a stomach of a patient. A control unit is adapted to drive the electrode set to apply to the body of the stomach a signal, configured such that application thereof increases a level of contraction of muscle tissue of the body of the stomach, and decreases a cross sectional area of a portion of the body of the stomach for a substantially continuous period greater than about 3 seconds"

Ben-Haim et al. in U.S. Pat. No. 6,571,127 disclose:

"The invention comprises methods of increasing contractile force and/or the motility of a GI tract. A first method comprises selecting a portion of the GI tract and applying a non-excitatory electric field to the portion, which field increases the force of contraction at the portion."

Lam T K et al. Hypothalamic sensing of circulating fatty acids is required for glucose homeostasis. Nature Medicine 3:320-327, 2005 disclose: "Here we postulate that physiological increments in plasma fatty acids can be sensed within the hypothalamus and that this sensing is required to balance their direct stimulatory action on hepatic gluconeogenesis."

Leitao C B et al. Lipotoxicity and decreased islet graft survival. Diabetes Care 33; 658-660, 2010 disclose: "Higher baseline triglycerides are associated with earlier decline in islet graft function."

PCT/IL2011/000116 filed on Feb. 1, 2011 discloses: "Apparatus (18) for treating a human patient, which includes one or more electrode contact surfaces (100), which are configured to be applied to a fundus (22) of the patient. A control unit (90) is configured to drive the one or more electrode contact surfaces (100) to apply an electrical signal to the fundus (22) that chronically improves a blood glucose level of the patient, in order to treat the patient, without calculating an impedance of tissue of the fundus (22) based on a sensed parameter that varies in response to the electrical signal, for detecting eating by the patient or a characteristic of food eaten by the patient."

Additional background art includes:

U.S. Pat. No. 7,840,269

US patent application 2009/0281449

Matthews et al. (1985) "Homeostasis model assessment: insulin resistance and B-cell function from fasting plasma glucose and insulin concentrations in man." Diabetologia 28: 412-9.

SUMMARY OF THE INVENTION

An aspect of some embodiments of the invention relates to selecting patients for treatment according to triglyceride levels. Optionally, patients have type 2 diabetes. Alternatively or additionally, patients are overweight. Alternatively or additionally, patients have relatively higher levels of blood pressure. Optionally, the triglyceride levels are adjusted before and/or during the treatment. Optionally or alternatively, relatively low triglyceride levels are maintained during treatment. Optionally or alternatively, treatment is selected and/or modified according to the triglyceride levels.

There is provided in accordance with an exemplary embodiment of the invention a method of treating a diabetic patient comprising:

measuring a triglyceride level in the diabetic patient;

selecting the patient for treatment according to the triglyceride level being below a threshold; and applying the treatment to the selected patient, the treatment comprising at least one of intra-abdominal and gastric electrical stimulation.

In an exemplary embodiment of the invention, the applying comprises applying the treatment to reduce an HbA1c level by at least 1.0% after 3 months of the treatment.

In an exemplary embodiment of the invention, the diabetic patient is a type 2 diabetic patient.

In an exemplary embodiment of the invention, n the threshold comprises a triglyceride level<=150 mg/dl. Alternatively, the threshold comprises a triglyceride level<=120 mg/dl. Alternatively, the threshold comprises a triglyceride level<=180 mg/dl.

In an exemplary embodiment of the invention, the applying comprises applying the diabetes treatment according to a function of triglyceride levels and expected effects of treatment.

In an exemplary embodiment of the invention, the triglyceride level comprises a fasting plasma triglyceride level.

In an exemplary embodiment of the invention, the method further comprises reducing the triglyceride level in the patient during at least one of before and during the treatment. Optionally, reducing comprises administering at least one drug. Optionally, at least one drug comprises selecting from the group consisting of: statin, fibrate, niacin. Alternatively or additionally, the reducing comprises at least one dietary change. Optionally, the at least one dietary change comprises selecting from the group consisting of: reducing fat, reducing carbohydrates, increasing omega-3 fatty acids, reducing alcohol.

In an exemplary embodiment of the invention, the method further comprises monitoring changes in the triglyceride level during the treatment; and adjusting the treatment parameters according to the changes.

In an exemplary embodiment of the invention, the method further comprises monitoring the triglyceride level during the treatment; and maintaining the triglyceride level below the threshold.

In an exemplary embodiment of the invention, the method further comprises monitoring an effect of the treatment; and administering triglyceride lowering treatment according to the effect.

In an exemplary embodiment of the invention, the method further comprises:

measuring a glycemic level in the diabetic patient;

selecting the patient for treatment according to the glycemic level being above a glycemic threshold;

applying the treatment to the selected patient to reduce the glycemic level.

Optionally, the glycemic level comprises an HbA1c level>=8%.

In an exemplary embodiment of the invention, the method further comprises selecting the patient for treatment according to the patient taking at least one oral diabetes medication. Optionally, at least one oral diabetes medication comprises one or more of; insulin, GLP-1 receptor agonist therapy, oral antidiabetic agent.

In an exemplary embodiment of the invention, the method further comprises:

measuring a weight of the diabetic patient;

selecting the patient for treatment according to the weight level being above a weight threshold; and applying the treatment to the selected patient to reduce the weight.

Optionally, the weight threshold comprises a BMI>=25.0 kg/m$^2$. Optionally or additionally, reduce weight comprises reduce weight by at least 5 kg after 6 months of the treatment.

In an exemplary embodiment of the invention, the method further comprises:

calculating a HOMA-IR of the diabetic patient to establish a baseline;

applying the treatment to the patient to reduce the HOMA-IR relative to the baseline.

Optionally, applying comprises applying the treatment to reduce the HOMA-IR by at least about 2.0 points after about 6 months of the treatment.

In an exemplary embodiment of the invention, applying comprises applying to extend life of beta cells.

In an exemplary embodiment of the invention, the method further comprises:

measuring a blood pressure of the diabetic patient;

selecting the patient for treatment according to the blood pressure being above at least one of a systolic and a diastolic threshold; and applying the treatment to the selected patient to reduce the blood pressure.

Optionally, the systolic threshold comprises 130 mmHg and the diastolic threshold comprises 80 mmHg.

In an exemplary embodiment of the invention, the method further comprises:

measuring an insulin/glucose ratio of the diabetic patient to establish a baseline;

applying the treatment to the selected patient to increase the insulin/glucose ratio relative to the baseline.

There is provided in accordance with an exemplary embodiment of the invention a method of weight loss comprising:

measuring a triglyceride level in an obese patient;

selecting the patient for treatment according to the triglyceride level being below a triglyceride threshold; and applying the treatment to the selected patient to reduce weight by at least about 5.0 kg after about 6.0 months of the treatment, the treatment comprising at least one of intra-abdominal and gastric electrical stimulation.

In an exemplary embodiment of the invention, the triglyceride level<=150 mg/dl.

There is provided in accordance with an exemplary embodiment of the invention a method of treating hypertension comprising:

measuring a triglyceride level in a patient with hypertension;

selecting the patient for treatment according to the triglyceride level being below a triglyceride threshold; and applying the treatment to the selected patient to reduce at least one of systolic and diastolic blood pressure, the treatment comprising at least one of intra-abdominal and gastric electrical stimulation.

In an exemplary embodiment of the invention, the triglyceride level<=150 mg/dl.

There is provided in accordance with an exemplary embodiment of the invention an apparatus for patient medical therapy comprising:

at least one electrode sized and shaped for contacting at least one of abdominal and gastric tissue;

a controller, the controller in electrical communication with the at least one electrode, the controller programmed to deliver electrical stimulation to the tissue; and a memory in electrical communication with the controller, the memory indicates a triglyceride level of the patient with one or more treatment parameters of the electrical stimulation.

In an exemplary embodiment of the invention, the memory further comprises an indication between the triglyceride level with drug treatment parameters, and apparatus is used in combination with the administration of drugs. Optionally, the memory is implanted. Alternatively or additionally, the memory is externally located and communicates with the controller by a programmer.

In an exemplary embodiment of the invention, the apparatus is packaged with instructions.

There is provided in accordance with an exemplary embodiment of the invention a method of reducing insulin resistance in a patient comprising:

measuring a triglyceride level in the patient;

selecting the patient for treatment according to the triglyceride level being below a threshold; and applying the treatment to the selected patient, the treatment comprising at least one of intra-abdominal and gastric electrical stimulation so that the insulin resistance is improved in the patient.

In an exemplary embodiment of the invention, the threshold comprises a triglyceride level<=150 mg/dl.

There is provided in accordance with an exemplary embodiment of the invention a method of improving an insulin/glucose ratio in a patient comprising:

measuring a triglyceride level in the patient;

selecting the patient for treatment according to the triglyceride level being below a threshold; and applying the treatment to the selected patient, the treatment comprising at least one of intra-abdominal and gastric electrical stimulation so that the insulin/glucose ratio is improved in the patient.

In an exemplary embodiment of the invention, the threshold comprises a triglyceride level<=150 mg/dl.

There is provided in accordance with an exemplary embodiment of the invention a method of treating a diabetic patient comprising:

measuring a triglyceride level in the diabetic patient;

providing a medicament to reduce the triglyceride level in the patient during at least one of before and during the treatment;

applying the treatment to the selected patient, the treatment comprising at least one of intra-abdominal and gastric electrical stimulation, the treatment selected according to the modified triglyceride level.

In an exemplary embodiment of the invention, the threshold comprises a triglyceride level<=150 mg/dl.

There is provided in accordance with an exemplary embodiment of the invention a method of treating a diabetic patient comprising:

modifying a treatment according to a triglyceride level of said patient, said treatment comprising at least one of intra-abdominal and gastric electrical stimulation. In an exemplary embodiment of the invention, modifying comprises selecting the treatment according to said triglyceride level.

In an exemplary embodiment of the invention, the method further comprises modifying said triglyceride level of said patient.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system and/or as a plurality of firmware instructions being executed on a microcontroller. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic or optical hard-disk and/or removable media and/or flash (e.g., solid-state) memory, for storing instructions and/or data. Optionally, a network connection is provided as well which may be direct connected or wireless. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
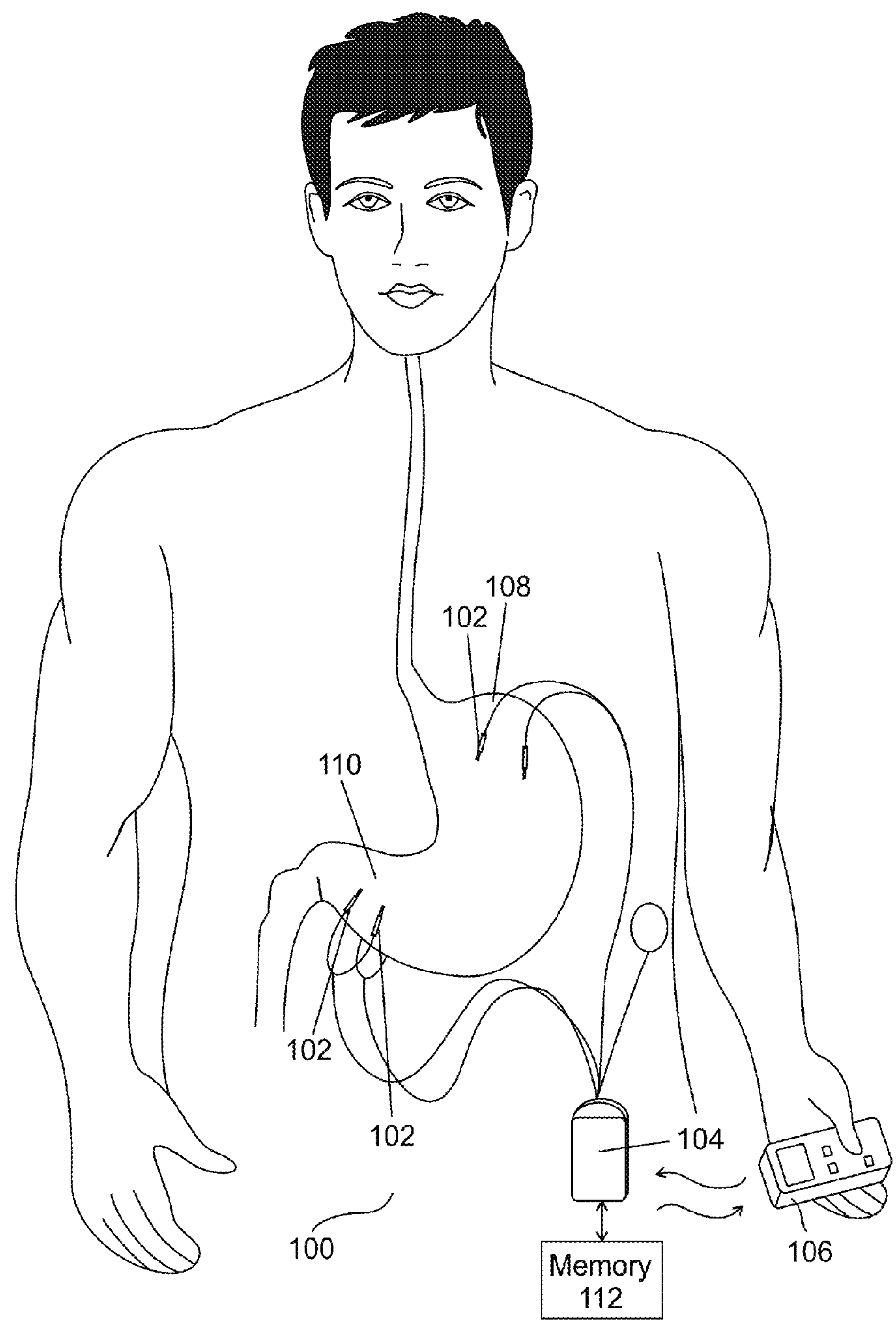
FIG. 1 is an illustration of the use of a gastric stimulatory device, in accordance with an exemplary embodiment of the invention.

The present invention, in some embodiments thereof, relates to a method of treating patients and, more particularly, but not exclusively, to a method of treating patients according to triglyceride levels.

An aspect of some embodiments of the invention relates to a method of treating patients, comprising selecting patients according to triglyceride levels, (e.g., fasting plasma triglyceride levels). Optionally, patients having triglyceride levels below a threshold are treated, for example, below 100 mg/dl, below 120 mg/dl, below 140 mg/dl, below 150 mg/dl, below 160 mg/dl, below 180 mg/dl, below 200 mg/dl, or other smaller, intermediate or larger values are used. Alternatively or additionally, a table is used, for example, patients having a triglyceride level in ranges (e.g., 141 mg/dl to 150 mg/dl; 151 mg/dl to 160 mg/dl) are selected and/or treated according to the parameters in the table. Alternatively or additionally, a function is used, for example, the function relates the triglyceride level of the patient to a type of treatment and/or parameters of treatment. Optionally, the threshold, table and/or function relate the triglyceride level of the patient to the expected effect of the treatment, for example, a function inversely relates the effect of decreasing HbA1c (e.g., for HbA1c values of 8.0% to 10.3%) by gastric electrical stimulation treatment, to the logarithm of the triglyceride level (e.g., from about 50 mg/dl to about 500 mg/dl). Optionally, the selected patients are treated, for example, by electrical stimulation.

Alternatively, in some embodiments, an indicator of triglycerides levels is measured, for example, as opposed to direct measurement of the triglyceride levels.

In an exemplary embodiment of the invention, the triglyceride level threshold is selected according to a desired and/or expected effect of treatment. Alternatively or additionally, the triglyceride level threshold is selected according to a sensitivity of treatment in achieving a desired and/or expected result.

In an exemplary embodiment of the invention, the patients are type 2 diabetic patients. Alternatively or additionally, one or more patients are pre-diabetic. Alternatively or additionally, patients are obese. Alternatively or additionally, patients have relatively higher systolic and/or diastolic blood pressure.

In an exemplary embodiment of the invention, the triglyceride levels of the patients are adjusted before the treatment starts. Alternatively or additionally, the triglyceride levels are adjusted during the treatment. Optionally, the triglyceride levels are reduced, for example, to be below the selection threshold. Alternatively or additionally, the triglyceride levels are reduced according to the effects of the treatment.

In an exemplary embodiment of the invention, the triglyceride levels of the patient are reduced and/or maintained for a period of time prior to treatment, for example, at least 3 months, at least 6 months, at least 12 months, or other smaller, intermediate or larger time frames are used. Optionally, the treatment time period is selected for example, according to a table of values indicating the length of reduced TG level and results.

In an exemplary embodiment of the invention, the relatively low triglyceride levels (e.g., the adjusted levels and/or unadjusted levels) are maintained during at least some of the treatment.

In an exemplary embodiment of the invention, the method of treatment is intra-abdominal stimulation, for example, gastric electrical stimulation. For example, stimulation of the pancreas, the stomach (e.g, fundus, antrum). Optionally, the method comprises providing a non-excitatory signal. Optionally or additionally, the method increases contraction responsiveness, for example, increasing the contraction force of stomach muscles. Optionally or additionally, the method relatively improves glycemic control. Optionally or additionally, the method relatively increases weight loss. Optionally or additionally, the method relatively improves insulin resistance. Optionally or additionally, the method relatively increases the life of beta-cells.

In an exemplary embodiment of the invention, the method relatively increases endogenous insulin secretion by beta-cells. Optionally, the increase in blood insulin level is measured per unit of blood glucose levels. In an exemplary embodiment of the invention, a relatively higher insulin/glucose ratio suggests that relatively more insulin is secreted (by the pancreas of the patient)_per unit of glucose than before treatment. Alternatively or additionally, the relatively higher ratio suggests that glucose is further reduced, for example, due to the stimulation and/or other mediators of glucose uptake factors. Alternatively or additionally, the relative higher ratio suggests that insulin resistance of the patient (e.g., of peripheral tissues) has decreased. In some cases, both insulin and glucose change. In some cases, only one of insulin or glucose change without substantial change to the other. For example, the increase is greater than 0%, or greater than about 10%, or greater than about 20%, or greater than about 25%, or greater than about 30%, or greater than about 40%, or greater than about 50%, or greater than about 70%, or greater than about 100%, or other intermediate or larger increases. Optionally, treatment by electrical stimulation is adjusted, for example, according to a table that indicates the desired improvement with the stimulation.

Optionally, the increase is compared to a baseline after treatment of, for example, about 3 months, about 6 months, about 12 months, about 18 months, about 24 months, or other smaller, intermediate or larger time frames are used.

In some embodiments, the insulin response is affected, for example, the change in the glucose rise. Optionally, as insulin naturally increases (e.g., due to rising blood glucose), the treatment further increases the insulin level. Alternatively or additionally, the insulin response is not changed (e.g., insulin rises similarly as without the treatment) by the treatment, but the reduction in the rise of the glucose is changed by the treatment.

In an exemplary embodiment of the invention, patients are selected independently of their glycemic levels, for example, the glycemic level is uncontrolled. Optionally, the HbA1c level measured in the patients is greater than or equal to 7%, greater than or equal to 7.5%, greater than or equal to 8%, greater than or equal to 8.5%, greater than or equal to 9%, or other smaller intermediate or larger cutoff values are used. Optionally or additionally, the HbA1c level is <=10.5%. In an exemplary embodiment of the invention, patients are selected according to the HbA1c levels. In some embodiments, the HbA1c level is measured prior to selection. Alternatively or additionally, the HbA1c level is measured after selection. Optionally or alternatively, the HbA1c level is measure throughout treatment, for example, to monitor the effectiveness of the treatment.

In an exemplary embodiment of the invention, electrical treatment is selected to reduce HbA1c levels by at least 1.0%, or at least 1.2%, or at least 1.4%, or at least 1.6%, or at least 1.8%, or at least 2.0%, or at least 2.2%, or at least 2.5%, or at least 3%, or at least 3.5%, or at least 4%, or other intermediate or larger percentages. HbA1c levels are reduced after about 3 months, or about 6 months, or about 12 months of treatment compared to baseline, or other smaller, intermediate or larger time frames. In one example, a table is used to select the electrical treatment based on the desired reduction in HbA1c levels.

In an exemplary embodiment of the invention, patients are on at least one oral antidiabetic agent. Alternatively or additionally, patients are on insulin therapy. Alternatively or additionally, patients are on Glucagon Like Peptide-1 (GLP-1) receptor agonist therapy.

In an exemplary embodiment of the invention, the treatment plan is selected according to the triglyceride level. Optionally, patients are treated if the triglyceride is below the threshold, for example, if the triglyceride level is below the threshold for a given period of time, for example, for 3 months, or 6 months, or 12 months, or other smaller, intermediate or larger time frames. Optionally or alternatively, patients having a triglyceride level above the threshold are also treated to reduce the triglyceride level as part of the treatment plan. In some embodiments of the invention, the triglyceride level of the patients is monitored to estimate and/or determine the efficacy of treatment.

In an exemplary embodiment of the invention, parameters of the treatment plan are set and/or adjusted according to the triglyceride level, for example, parameters of the treatment plan are based on the treatment table, such as having correlation data obtained by trial and error. One or more examples of treatment parameters that are adjusted taking into account the triglyceride level include; eating detection parameters, duration of therapy per meal, signal amplitude, change in mixture and/or balance of signal types, switching treatment on or off. Further details of adjustment will be provided for example, with reference to the section "METHOD OF CHOOSING A TREATMENT". Optionally, parameters are adjusted before the start of treatment. Optionally or additionally, parameters are adjusted during the treatment, for example, using feedback of one or more measurements of the triglyceride levels.

An aspect of some embodiments of the invention relates to a method of screening patients (e.g., type 2 diabetics) for medical treatment. In an exemplary embodiment of the invention, the method comprises measuring a triglyceride level in the type 2 diabetic patient and treating the patient, such as according to a table of methods and/or algorithms for different triglyceride levels.

An aspect of some embodiments of the invention relates to a method of selecting overweight and/or obese patients for weight loss treatment. In an exemplary embodiment of the invention, the method comprises measuring a triglyceride level in the patient and treating the patient, such as according to a table of methods for different triglyceride levels.

In an exemplary embodiment of the invention, patients are selected for electrical treatment to reduce weight by at least 4.5 kg, or at least 5.0 kg, or at least 5.5 kg, or at least 6.0 kg, or at least 6.5 kg, or at least 10 kg, or at least 15 kg, or other intermediate or larger percentages. Weight is reduced after about 3 months, or about 6 months, or about 12 months of treatment compared to baseline, or other smaller, intermediate or larger time frames. For example, the selection is done according to a table associating the electrical treatment with the desired weight loss.

An aspect of some embodiments of the invention relates to a method of relatively improving insulin resistance, for example, as measured by the homeostatic model assessment of insulin resistance (HOMA-IR) as described by Matthews et al. (1985) Diabetologia 28: 412-9, incorporated herein by reference in its entirety. Improvements in HOMA-IR are, for example, a reduction of about 2 units, about 3 units, about 4 units, about 5 units (e.g., from about 10 units to about 7 units, to about 5 units), or other smaller, intermediate or larger time frames. Improvements in HOMA-IR are, for example, compared to a baseline after treatment of about 3 months, 6 months, 12 months, or other smaller, intermediate or larger time frames. In an exemplary embodiment of the invention, the method comprises measuring a triglyceride level in the patient and treating the patient, such as according to a table of methods for different triglyceride levels. Alternatively or additionally, the triglyceride level in the patient is reduced before and/or during the treatment. In one example, electrical treatment is applied according to a table associating the treatment with the desired reductions in HOMA-IR levels.

Alternatively or additionally, the insulin/glucose ratio (e.g., as described herein) is used as a measure of improvement in insulin resistance.

An aspect of some embodiments of the invention relates to a method of treating type 2 diabetic patients. In an exemplary embodiment of the invention, the method comprises reducing a triglyceride level in a diabetic patient before treatment, for example, by abdominal and/or gastric electrical stimulation. Optionally or additionally, the reduction occurs during the treatment. Optionally, the triglyceride level is reduced to be below a threshold.

An aspect of some embodiments of the invention relates to a method of treating type 2 diabetic patients according to triglyceride levels, for example, using abdominal and/or gastric stimulation. In an exemplary embodiment of the invention, the method comprises setting treatment parameters according to a measured triglyceride level. For example, patients with relatively higher TG levels might require relatively greater amounts (e.g., intensity, frequency) of electrical therapy to respond reasonably. Optionally, treatment parameters are adjusted and/or modulate during the treatment according to monitored triglyceride levels. For example, once the TG level is reduced enough, a relatively lower dose of electrical therapy will be sufficient to be effective. Optionally, the adjustment and/or modulation is done to achieve a desired performance.

In some embodiments, the TG level is reduced to be below a threshold, for example, 120 mg/dl, 150 mg/dl, 180 mg/dl, or other smaller, intermediate or larger values. Alternatively, the TG level is reduced by a value, for example, by about 10 mg/dl, or about 20 mg/dl, or about 30 mg/dl, or about 50 mg/dl, or about 100 mg/dl, or other smaller, intermediate or larger values.

An aspect of some embodiments of the invention relates to a method of treating patients having relatively higher blood pressure (such as systolic and/or diastolic blood pressure) according to triglyceride levels. In an exemplary embodiment of the invention, the method comprises measuring a triglyceride level in the patient and treating the patient, such as according to a table of methods for different triglyceride levels.

An aspect of some embodiments of the invention relates to a method of reducing insulin resistance in a patient comprising measuring a triglyceride level in said patient, selecting said patient for treatment according to said triglyceride level being below a threshold; and applying said treatment to said selected patient, said treatment comprising at least one of intra-abdominal and gastric electrical stimulation so that said insulin resistance is improved in said patient. Alternatively or additionally, the insulin resistance is measured by the insulin/glucose ratio, where an improvement in the ratio is due to improved insulin resistance.

Overview

Selecting patients for medical treatment can be challenging, as predicting how one patient will respond to medical treatment is uncertain, for example, different patients potentially respond differently, even to the same treatment. Furthermore, once the treatment has been selected, adjusting the treatment to obtain relatively improved results can also be challenging. One example is trial and error, in which the patient with the medical condition is administered treatment such as based on clinical guidelines and/or the experience of the physician. The results of the treatment effects on the patient can then be observed. Based on the treatment results, the treatment can be maintained, removed, changed and/or another treatment added.

Inventors have conducted experiments with gastric electrical stimulation to treat type 2 diabetes and/or obesity. The results have been surprising. Inventors unexpectedly showed that patients that had a relatively lower fasting plasma triglyceride level had relatively improved glycemic responses to treatment (e.g., as manifested by a relatively larger decrease in HbA1c levels), weight loss, improvement in insulin resistance (e.g., as manifested by relatively lower HOMA-IR levels), systolic and/or diastolic blood pressure. The association of the treatment results with the triglyceride levels is surprising, as inventors are unaware of a similar effect with other antihyperglycemic agents and/or procedures.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Exemplary Treatment Device

For purposes of better understanding some embodiments of the present invention, as illustrated in FIGS. 2-6 of the drawings, reference is first made to the construction and operation of an exemplary treatment device, such as a surgically implantable gastric stimulatory device 100 (e.g., DIAMOND (TANTALUS) available by MetaCure) as illustrated in FIG. 1. Device 100 was designed and developed for use by type 2 diabetic patients. Device 100 can be used in patients that are inadequately controlled on combinations of oral agents, or device 100 can be used instead of oral therapy. Device 100 applies gastric stimulation. In an exemplary embodiment of the invention, the stimulation achieves an effect in the patient of feeling full relatively sooner after eating a meal. Empirical evidence (e.g., detailed in the section "EXPERIMENTAL RESULTS") supports the hypothesis that device 100 results in increased glycemic control (e.g., decreases HbA1c) and/or weight loss.

In an exemplary embodiment of the invention, device 100 comprises 3 pairs of bi-polar electrodes 102. Optionally, one pair of electrodes 102 is coupled to a fundus 108 of a patient's stomach. Alternatively or additionally, the electrodes are coupled to a cardia of the stomach. Alternatively or additionally, the electrodes are coupled to a corpus of the stomach. Another pair of electrodes 102 is coupled to an anterior antrum 110 of the stomach, and the last pair of electrodes 102 is coupled to a posterior antrum 110. Some not necessarily limiting examples of contact between the electrodes and the tissue include; suturing the electrode to the tissue, grasping the tissue with the electrode, gluing the electrode to the tissue, piercing the tissue with the electrode.

In some embodiments, electrodes are flat for contacting the tissue (e.g., circular, rectangular). Alternatively, electrodes are needles for piercing the tissue. Optionally, electrodes have a surface area large enough to allow current to pass to the tissue without damaging the tissue. In an exemplary embodiment of the invention, electrodes are made out of a suitable electrically conductive biocompatible material, for example, stainless steel.

In some embodiments, fewer electrodes 102 can be used, for example, two pairs, one pair, and/or a single electrode. In the case of the single electrode, the casing of device 100 can act as the ground.

In an exemplary embodiment of the invention, device 100 comprises a pulse generator 104. Electrodes 102 are connected to pulse generator 104. Generator 104 is implanted in a surgically created pocket in the anterior abdominal subcutaneous fat. Alternatively, generator 104 is implanted in the intraperitoneal space on and/or near the stomach.

In an exemplary embodiment of the invention, device 100 comprises an external programmer 106. In an exemplary embodiment of the invention, programmer 106 and/or generator 104 have telemetry capabilities, for example, allowing remote programming by the patient themselves or by any other person assisting the user, for example, the patient's physician. In an exemplary embodiment of the invention, programmer 106 charges generator 104.

In an exemplary embodiment of the invention, device 100 is coupled to a memory 112, for example, memory 112 is stored thereon, memory 112 is stored on programmer 106 and/or memory 112 is remotely accessible, for example, by a wireless connection.

In an exemplary embodiment of the invention, device 100 is implanted into a patient by laparoscopic surgery. Alternatively, device 100 is implanted by endoscopic methods.

In an exemplary embodiment of the invention, device 100 is designed to modulate gastric contractions. Pulse generator 104 is programmed to detect food intake (e.g., eating) by fundal 108 and/or antral 110 electrodes 102. Fundal 108 and/or antral 110 electrodes 102 trigger pulse generator 104 to provide electrical stimulation (e.g., electrical pulse) to antrum 110 using at least one pair of electrodes 102 located on the antrum. In some embodiments of the invention, food-mediated stimulation continues for about 90 minutes after activation. In some embodiments of the invention, food-mediated stimulation continues in an on-and-off fashion for about 90 minutes after activation.

In an exemplary embodiment of the invention, the electrical pulse is a non-excitatory signal (e.g., delivered during the refractory period of the normal action potential). The electrical pulse causes an increase in the amplitude of the contraction force without changing the rate of contractions. The increase in contraction force is believed to increase the afferent signals to the central nervous system (e.g., through the vagus nerve and/or other nerves innervating the stomach). The result is believed to be increased metabolic activity and early meal cessation (e.g., enhancement of the body's response to food intake leading to satiety). Without being bound to theory, these effects suggest a central nervous system mediated action which is similar to that of glucagon-like peptide-1 (GLP-1) receptor agonists (e.g., improvement in glycemic control, weight and blood pressure). Some examples of differences include no gastrointestinal side effects, and/or an increase rather than a delay in gastric emptying.

In an exemplary embodiment of the invention, the electrical stimulation signal is set by programmer 106 during the initial installation of device 100 in the patient. Optionally, programming occurs one to two weeks after the implantation surgery.

In an exemplary embodiment of the invention, generator 104 has an internal power source such as a battery. Optionally, the battery of pulse generator 104 is rechargeable (e.g., weekly for up to one hour) with an external charger, for example, programmer 106 charges the battery of generator 104.

In an exemplary embodiment of the invention, use of device 100 causes relatively increased glycemic control (e.g., by relatively lowering HbA1c values). In some embodiments, use of device 100 results in weight loss for example, about 3 kg, about 4 kg, about 5 kg, about 6 kg, or other smaller, intermediate or larger amounts of weight loss. In some embodiments, use of device 100 results in reducing diastolic and/or systolic blood pressure, for example, about 19.7 mmHg in systolic blood pressure and/or about 10.2 mmHg in diastolic blood pressure. Weight loss and/or blood pressure reductions occur over 3 months of treatment, or 6 months, or 12 months, or other smaller, intermediate or larger lengths of time.

In an exemplary embodiment of the invention, the electrical therapy is selected to achieve the desired improvements, for example, according to a table associating treatments with the desired results.

In an exemplary embodiment of the invention, the treatment is administered by device 100 according to logic (e.g., a software module), for example using a table. Optionally, the table is stored on memory 112. In an exemplary embodiment of the invention, the table contains treatment parameters correlated with triglyceride levels. One or more non-limiting examples of treatment parameters, such as device 100 parameters of the non-excitatory stimulatory pulse include; amplitude, time duration, time delay, frequency, waveform. Optionally, other parameters are correlated by the table, for example, the sensitivity to food intake (and/or food type) is correlated with therapy delivery parameters. Optionally, the treatment parameters are based on trial and error, for example, empirical data collected from the patient with implanted device 100 (e.g., during the treatment) and/or previously collected from a group of patients such as part of an experiment.

In an exemplary embodiment of the invention, one or more inputs are used to control the therapy delivery, for example, through programmer 106. Not necessarily limiting examples include; programming as described above, internal sensor input (e.g., measuring TG levels, insulin levels, glucose levels or other parameters), external sensor input (e.g., blood pressure, weight), physician an/or user controlled for manually providing treatment parameters (e.g., intensity, frequency). Optionally, the input provided is used to determine the therapy according to the desired change, for example, by using the correlation table.

In some embodiments, adjustments are manual. For example, the physician and/or user can adjust treatment according to sensitivity to food intake (and/or food type). Alternatively, the adjustments are partly manual and partly automatic, for example, the user manually approving changes due to sensor data (e.g., measured weight, with the weight being sensed by the sensor and wirelessly transmitted to the device).

In some embodiments of the invention, device 100 is part of a drug-device combination, for example, for treating type 2 diabetic patients. In some embodiments, treatment is planned according to a combination treatment by device 100 and by one or more drugs (e.g., insulin, oral agents). One or more non-limiting examples of the administration of drugs include, orally, by device 100, by a drug administering device (e.g., insulin pump). One or more non-limiting examples of drug treatment parameters include; the drug type, the drug dose, the drug administration schedule over time, the route of administration. Optionally, the logic (e.g., on memory 112) stores the combined treatment parameters for device 100 and for the administration of drugs. One or more non-limiting examples of the function of the drug-device combination include; device 100 or drugs compensating for the other, device 100 and/or drugs working synergistically, increasing the use of device 100 and/or drugs according to the effects of treatment of the other. For example, if device 100 has not lowered HbA1c sufficiency, the dose of the oral agent can be increased.

In an exemplary embodiment of the invention, software for patient selection and/or therapy modification in response to triglyceride levels is provided (e.g., to perform the selection and/or modification as described herein). Optionally, the software is compatible with device 100 and sold together (stored on memory 112 and/or provided separately on a CD-ROM), or is available separately (e.g., for download). In an exemplary embodiment of the invention, the software comprises a module for controlling treatment according to the triglyceride level. Optionally, the software comprises a module for selecting patients according to the triglyceride level. Optionally or additionally, the software comprises a module for adjusting treatment according to changing triglyceride levels.

In an exemplary embodiment of the invention, device 100 is packaged with instruction to do one or more of the following not necessarily limiting functions; install device, program device, select patients, adjust therapy, use software.

Further details of the structure and/or function of device 100, in accordance with some embodiments, can be found, for example, with reference to the following patent applications, incorporated herein by reference in their entirety:

U.S. Pat. No. 6,571,127 which describes a method of increasing a contractile force and/or motility of a GI tract;

U.S. Pat. No. 7,512,442 which describes an apparatus for treating a condition such as obesity;

U.S. Pat. No. 7,840,269 which describes an apparatus for detecting when a patient swallows, and the type and amount of matter ingested; and US patent application 2009/0281449 which describes a method for optimization of thresholds for eating detection.

Exemplary Signals

A non-limiting example of signals provided by device 100 and/or methods of analyzing the signals (e.g., impedance calculations) are described for example, with reference to PCT/IL2011/000116, incorporated herein by reference. For the convenience of the reader, some of the descriptions from the reference are also provided below.

In an exemplary embodiment of the invention, the electrical signal generated by a control unit (e.g., generator 104) may have a variety of parameters and/or properties, including with regard to its shape, duty cycle, frequency, duration, offset, and combination of pulses. For some applications, the control unit drives the electrode (e.g., electrodes 102) contact surfaces to apply the electrical signal as a plurality of pulses. For some applications, the control unit configures one or more of the pulses (such as a majority of the pulses, or all of the pulses) to have one or more of the following parameters:

- a pulse width of at least 1 microsecond, no more than 2 seconds, and/or between 1 microsecond to 2 seconds (e.g., at least 2 microseconds, no more than 5 milliseconds, and/or between 2 microseconds and 5 milliseconds), such as at least 5 microseconds, no more than 100 milliseconds, and/or between 5 microseconds and 100 milliseconds, e.g., at least 10 microseconds, no more than 10 milliseconds, and/or between 10 microseconds and 10 milliseconds, such as at least 15 microseconds, no more than 5 milliseconds, and/or between 15 microseconds and 5 milliseconds, e.g., at least 20 microseconds, no more than 1 millisecond, and/or between 20 microseconds and 1 millisecond, such as at least 25 microseconds, no more than 100 microseconds, and/or between 25 and 100 microseconds, for example, about 30 microseconds, or between 5 msec and 10 msec (e.g., 6 msec/phase), or 50 microseconds to 70 microseconds (e.g., 61 microseconds);
- a voltage of no more than 10 volts, such as at least 0.5 volts, e.g., at least 1.25 volts, no more than 4.1 volts, and/or between 1.25 and 4.1 volts, e.g., 3.5 volts;
- an amplitude of at least 0.1 mA, no more than 100 mA, and/or between 0.1 mA and 100 mA, typically at least 5 mA (e.g., at least 10 mA), no more than 35 mA, and/or between 5 mA (e.g., 10 mA) and 35 mA, for example, about 10-13 mA, or about 15-20 mA (which depends on the tissue impedance) (because an amplitude of greater than between 13 and 15 mA usually (but not always) is felt by the patient, it is generally desirable to limit the amplitude to no more than the sensation threshold of the particular patient). For example, in an extreme case, tissue impedance (electrode-tissue interface impedance) may be as high as 700 ohms; in this case, if voltage of 3.5 volts is applied, the current is 5 mA;
- pulses that are uniphasic or biphasic (with or without a gap between the two phases or consecutive pulses). In pulses with gaps between phases, the gap is, for example, about 0.1 msec to about 0.5 msec, or about 0.2 msec to about 0.3 msec, or other smaller, intermediate or larger times.
- pulses that are substantially square, saw tooth, sinusoidal, exponential, ramping, triangular, capacitor discharge (approximately exponential), having sharp or gradual gradients, symmetric or asymmetrical, or a combination of these properties;
- a pulse frequency of at least 1 Hz, such as at least 10 Hz 5 or 20 Hz, no more than 100 Hz (e.g., 85 Hz), or at least one pulse per second, five pulses per second, ten pulses per second, or 20 pulses per second, and/or no more than 100 pulses per second;
- pulses per contraction (e.g., Antrum), of about 10 pulses per contraction, or about 50 pulses, or about 100 pulses, or about 150 pulses, or about 200 pulses, or other smaller, intermediate or larger numbers of pulses per contraction;
- timing of the application of pulses, for example; continuous application, or after meals (e.g., synchronized to natural stomach rate);
- an energy per pulse (e.g., an average energy per pulse) of at least 0.05 microjoules, no more than 50 microjoules, and/or between 0.05 and 50 microjoules, such as at least 0.1 microjoules, no more than 5 microjoules, and/or between 0.1 and 5 microjoules; and/or an instantaneous power of at least 0.1 milliwatts, no more than 500 milliwatts, and/or between 0.1 milliwatts and 500 milliwatts, such as at least 5 milliwatts, no more than 100 milliwatts, and/or between 5 milliwatts and 100 milliwatts.

For some applications, the pulses are applied in a plurality of pulse trains, one or more of which trains (such as a majority or all) typically has one or more of the following parameters:

a total duration of each train of pulses of at least 0.1 seconds, no more than 5 seconds, and/or between 0.1 and 5 seconds, such as at least 0.5 seconds, no more than 2 seconds, and/or between 0.5 and 2 seconds;

a number of pulses per train of at least 1, no more than 100,000, and/or between 1 and 100,000, such as at least 100, no more than 20,000, and/or between 100 and 20,000; and/or the pulse train can last, for example, about 5 minutes, about 10 minutes, about 15 minutes, about 20 minutes, about 30 minutes, or other smaller, intermediate or larger time periods. In some embodiments, during a treatment the pulse trains vary in length, for example, the first pulse train lasts 15 minutes, and subsequent pulse trains last 10 minutes;

a gap between the pulse train periods lasting, for example, about 5 minutes, about 10 minutes, about 15 minutes, about 20 minutes, about 30 minutes, or other smaller, intermediate or larger time periods;

the number of pulse trains per session (e.g., trains separated by the pulses), for example, about 1 train, or about 2, or about 4, or about 6, or about 10, or other intermediate or larger number of pulse trains;

biphasic pulses, such as described hereinbelow.

For some applications in which the pulses are uniphasic, the phase of the pulses alternates from time to time (e.g., once every several seconds (e.g., one minute) to every 24 hours, or once every one or more physiological cycles of the tissue to which the electrode contact surfaces are coupled) between positive and negative pulses. For some applications, a trailing balancing phase is provided after one or more of the pulses. Use of such alternating phases and/or trailing balancing phase may reduce the effect of polarization of the electrode contact surfaces.

For some applications, biphasic signals are provided in accordance with an application of the present invention. Each pulse includes a positive phase and a negative phase; the positive phase may precede or follow the negative phase. For some applications, each of the phases has a duration of at least 1 usec, no more than 500 usec, and/or between 1 and 500 usec, such as at least 10 usec, no more than 100 usec, and/or between 10 and 100 usec, e.g., 30.5 usec or 61 usec (optionally, the duration is selected based on the measured tissue impedance, i.e., electrode-tissue interface impedance). For some applications, the control unit, and/or a medical worker, sets the duration of the pulses at least in part responsively to measured tissue impedance, i.e., electrode-tissue interface impedance.

For some applications, each pulse includes a gap between the positive and negative phases, which typically has a duration of between 1 usec and 1 msec. The length of the gap may sometimes be constrained by performance of the circuitry (such as the amount of time necessary to open and close switches necessary for discharging a capacitor into the tissue), but for some applications may be programmable, such as between 0.1 usec and 100 msec, e.g., between 100 usec and 1 msec. For other applications, a gap is not provided between the phases.

For some applications, the biphasic pulses are applied at least 1 time, no more than 100 times, and/or between 1 and 100 times per second, such as at least 5 times, no more than 40 times, and/or between 5 and 40 times per second, e.g., 10 times per second. (The number of phases per second equals twice the number of pulses per second.) The pulses are typically applied continuously when the signal is applied.

In an exemplary embodiment of the invention, the device senses a parameter that varies in response to the applied electrical signal, and calculates, based on the sensed parameter, an impedance of tissue, such as the fundus. Optionally, (e.g., for some of the applications described above), the control unit is configured to configure one or more parameters of the electrical signal responsively to the calculated impedance.

In an exemplary embodiment of the invention, the impedance measuring signal is also therapeutic.

In an exemplary embodiment of the invention, one or more non-limiting examples of parameters of the signal timing within a treatment session (e.g., the 90 minute session) include;

6 msec of signal (e.g., positive and/or negative)

6 msec of the rest state (e.g., 50%)

Total signal time=1.2 msec (e.g., 6 msec of signal delivery+6 msec of rest)

A train of 100 pulses for a total signal time of 0.6 seconds (e.g., 6 msec×100)

If every 20 seconds there is one stomach cycle (eg., 3 cycles per minute), the effective on time is 0.6/20 (e.g., duty cycle) for the positive portion of the signal. A similar calculation can be made for the negative portion of the signal.

To calculate the effective signal applied during a session (e.g., 90 minutes), multiply 0.6/20 by 90 minutes, then multiply by 50% (e.g., because 90 minute sequence has 50% rest periods).

Exemplary Method of Treatment

Figure 2:
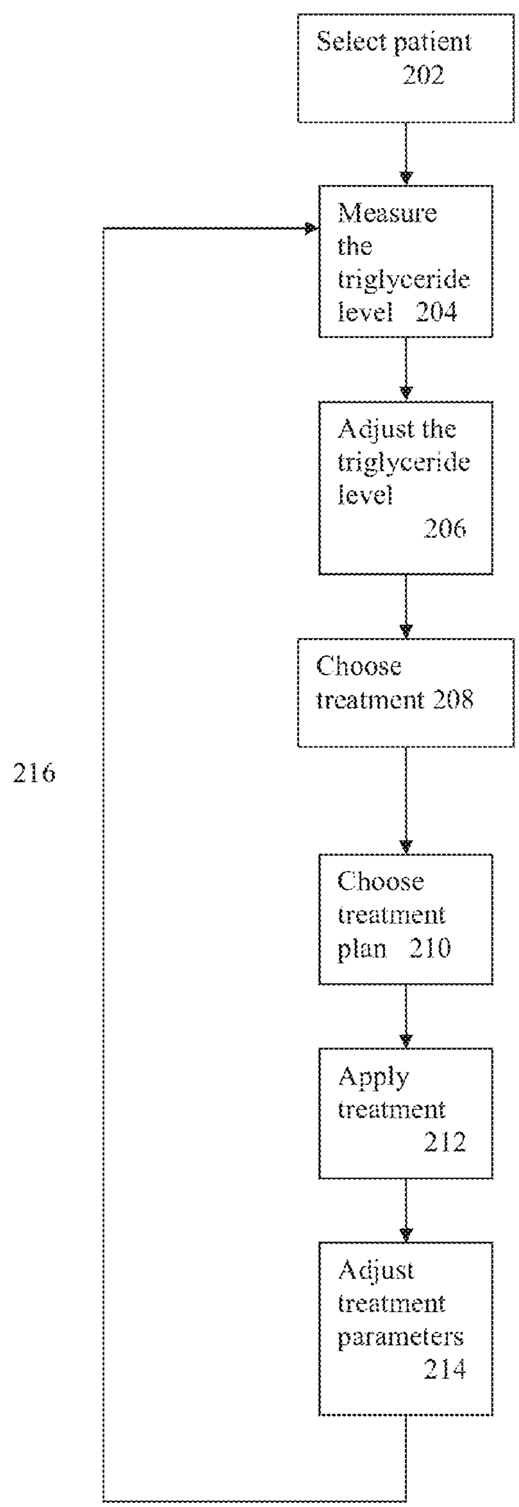
FIG. 2 is a flowchart of a method of treating patients, in accordance with an exemplary embodiment of the invention.

FIG. 2 is a flowchart of a method of treating patients (e.g., type 2 diabetics) while taking triglyceride levels into account, in accordance with an exemplary embodiment of the invention. Optionally, the method comprises screening patients for treatment. Alternatively or additionally, the method comprises reducing the triglyceride level as part of the treatment. Alternatively or additionally, the method comprises selecting and/or adjusting treatment parameters according to the triglyceride level.

At 202, a patient (e.g., with type 2 diabetes) is selected for treatment, in accordance with an exemplary embodiment of the invention. In an exemplary embodiment of the invention patients have been diagnosed with a disease that is treatable by the electrical stimulation therapy, for example type 2 diabetes (e.g., at various stages), obesity, hypertension. Optionally, the patients have been previously diagnosed, for example, by the physician. Alternatively, the patients are diagnosed as part of the therapy, for example, the diagnostic criteria including one or more measurement thresholds defined below. For example, a patient with HbA1c>=8% is diagnosed as having a condition treatable with the electrical stimulation, for example, independent of a clinical diagnosis.

Optionally, patients with inadequate glycemic control are selected, for example, patients with HbA1c levels>=7%, >=7.5%, >=8%, >=8.5%, >=9%, or other smaller, intermediate or larger threshold values are selected. Optionally or additionally, selected patients are being treated with at least one oral antidiabetic therapy. Optionally or additionally, selected patients are being treated with insulin therapy. Optionally or additionally, selected patients are being treated with GLP-1 receptor agonist therapy. Optionally or additionally, selected patients are being treated with triglyceride lowering therapy, for example, as described with reference to table 1.

In some embodiments of the invention, type 2 diabetic patients with relatively high insulin resistance (e.g., as measure by HOMA-IR) are selected for treatment, for example, to relatively improve insulin resistance. Optionally, selected patients have HOMA-IR values>=6.0, >=8.0, >=10.0, or other smaller, intermediate and/or larger values are used.

In some embodiments of the invention, overweight and/or obese patients are selected, for example, patients having a body mass index (BMI) of greater than 25.0 kg/m$^2$, greater than 30.0 kg/m$^2$, greater than 40.0 kg/m$^2$, or other smaller, intermediate or larger values are used. Alternatively, other measures of obesity are used, for example, skin fold thickness, waist circumference and waist to hip ratio, bio-impedance. Optionally, the overweight and/or obese patients are selected for weight loss treatment. Optionally, the overweight and/or obese patients are also type 2 diabetics. Alternatively, the overweight and/or obese patients do not have type 2 diabetes.

In some embodiments of the invention patients with relatively higher blood pressure are selected. Optionally, patients have a relatively high systolic blood pressure, for example, greater than 130 mmHg (such as for diabetics), greater than 140 mmHg, greater than 160 mmHg, or other smaller, intermediate or larger values are used. Alternatively or additionally, patients have a relatively high diastolic blood pressure, for example, greater than 80 mmHg (such as for diabetics), greater than 90 mmHg, greater than 100 mmHg, or other smaller, intermediate or larger values are used.

One or more non-limiting examples of oral diabetes medications include: a biguanide (e.g., increases sensitivity to insulin in the peripheral tissues) such as metformin, an insulin secretagogue (e.g., stimulates insulin release from beta cells) such as a sulfonylurea like glyburide, a thiazolidinedione (e.g., sensitizes peripheral tissues to insulin) such as rosiglitazone, an alpha-glucosidase inhibitor (e.g., decreases absorption of carbohydrates in the intestines) such as acarbose.

A non-limiting example of GLP-1 receptor agonist therapy is exenatide.

In some embodiments of the invention, patients are selected for improvements in endogenous insulin secretion, for example, as measured by blood insulin levels. In an exemplary embodiment of the invention, the insulin secretion is increased per unit of blood glucose levels. Optionally, the patients selected for treatment have a disease that is independent of insulin (e.g., patients with dysfunctional beta cells rather than patients with non-functional beta cells).

In some embodiments of the invention patients are selected for improvements in insulin resistance, for example, as measured by HOMA-IR and/or insulin/glucose (ratio). Optionally, the patients selected for treatment have a disease that is independent of insulin (e.g., patients with dysfunctional beta cells rather than patients with non-functional beta cells).

In an exemplary embodiment of the invention, type 2 diabetes is a clinical disorder. A non-limiting example of a definition is "a syndrome of disordered metabolism and inappropriate hyperglycemia secondary to an absolute/relative deficiency of insulin, or a reduction in biological effectiveness of insulin, or both." In an exemplary embodiment of the invention, pre-diabetes is a clinical disorder. A non-limiting example of a definition is according to diagnostic criteria, such as fasting blood glucose of 6.1-6.9 mmol/L and/or a 2 hour 75 gram oral glucose tolerance test of 7.8-11.0 mmol/L. In an exemplary embodiment of the invention, a non-limiting example of a definition of obesity is "the presence of abnormal absolute amount or relative proportion of body fat". In an exemplary embodiment of the invention, a non-limiting example of a definition of relatively higher systolic and/or diastolic blood pressure is as provided above.

At 204, the triglyceride level of the patients is measured, in accordance with an exemplary embodiment of the invention. In an exemplary embodiment of the invention, the triglyceride level is measured after the patient has fasted, for example, for at least 12 hours, for at least 14 hours, or other smaller, intermediate or larger number of hours. In an exemplary embodiment of the invention, the triglyceride level of the patient is measured directly, for example, by obtaining a venous blood sample, directly in the blood by inserting a fiber optic chemical sensor, by an implanted lab on chip that removes a blood sample and processes the sample.

In some embodiments of the invention, hepatic triglyceride levels are measured, for example, by a non-invasive method such as magnetic resonance imaging (MRI). Alternatively or additionally, the level of very-low-density-lipoproteins (VLDL) in the patient's blood is measured. Optionally, the hepatic triglyceride levels and/or VLDL levels are utilized similarly to plasma triglyceride levels, for example, in selecting patients, in selecting treatment, in selecting treatment parameters and/or in adjusting the levels. Optionally, hepatic triglyceride levels are used in combination with plasma triglyceride levels.

Optionally, at 206, the triglyceride level is adjusted, for example, as described with reference to the section "METHOD OF ADJUSTING TRIGLYCERIDE LEVELS", in accordance with an exemplary embodiment of the invention. Alternatively or additionally, the triglyceride level is adjusted before 204, for example, triglyceride levels are adjusted before being measured, such as for a patient already on triglyceride lowering medication. Alternatively or additionally, the triglyceride level is adjusted with treatment (e.g., as in 212), for example, if treatment does not work as well as expected, additional measures can be taken to further lower the triglyceride level if it is still relatively high (e.g., increase in drug dose, additional drugs). Alternatively or additionally, the relatively low triglyceride level (e.g., adjusted and/or unadjusted level) is maintained during treatment (e.g., as in 212), for example, patients continue taking their triglyceride lowering medications.

At 208, treatment is selected, in accordance with an exemplary embodiment of the invention. Optionally, the treatment provided is intra-abdominal stimulation, for example, electrical gastric stimulation by the gastric stimulatory device as described in the section "EXEMPLARY TREATMENT DEVICE".

Optionally, at 210, the treatment plan is selected according to the triglyceride level as measured in 204, in accordance with an exemplary embodiment of the invention, for example, as will be described with reference to the section "METHOD OF CHOOSING A TREATMENT".

In one example, treatments are chosen based on a table of TG cutoff values, for example, the table associating the treatment with desired outcomes. Optionally, the table is based on experimentally derived data, for example, as shown in the "EXAMPLES" section. Alternatively, theoretical considerations are used for selection of the TG cutoff value.

At 212, the treatment is applied, in accordance with an exemplary embodiment of the invention. Optionally, standard treatment is provided, (e.g., according to the device settings), such as device 100 parameters of the non-excitatory stimulatory pulse; amplitude, time duration, time delay, frequency, waveform, for example, as described in the section "EXEMPLARY TREATMENT DEVICE". Alternatively or additionally, treatment is provided according to the selected treatment plan as in 210.

In an exemplary embodiment of the invention, additional therapy is provided, for example, if TG levels are relatively high. Alternatively, therapy is reduced, for example, if TG levels are relatively low. Optionally, the relatively high and low threshold values are selected, for example, based on a table associating the treatment parameters with the results for different TG levels.

In some embodiments, treatment is experimentally adjusted up or down, and based on the response of the patient, the type of therapy is selected.

Optionally, at 214, the treatment parameters (e.g., as in 210) are adjusted, in accordance with an exemplary embodiment of the invention. Optionally, treatment parameters are adjusted according to a feedback loop 216 comprising of measuring the triglyceride level as in 204, and/or adjusting the triglyceride level as in 206, and/or adjusting treatment parameters according to the measured triglyceride level.

In an exemplary embodiment of the invention, any treatment parameters (e.g., when to apply the treatment, what triggers the treatment) are adjusted when TG levels (e.g., as measured in the feedback loop) change (e.g., up or down). For example, if TG levels increase during treatment, the treatment is increased, for example, according to a table of correlated values and parameters.

Further details of adjusting the parameters will be provided, for example, with reference to the section "METHOD OF CHOOSING A TREATMENT".

In an exemplary embodiment of the invention, a method of screening patients for treatment comprises, for example boxes 202, 204, and/or 212, for example, as will be described with reference to the section "METHOD OF SCREENING".

In an exemplary embodiment of the invention, a method of adjusting triglyceride levels as part of treatment comprises, for example boxes 202, 204, 206, and/or 212, for example, as will be described with reference to the section "METHOD OF ADJUSTING TRIGLYCERIDE LEVELS".

In an exemplary embodiment of the invention, a method of setting and/or adjusting parameters of treatment according to triglyceride levels comprises, for example boxes 202, 204, 208, 210, 212, 214 and/or 216, for example, as will be described with reference to the section "METHOD OF CHOOSING A TREATMENT".

Method of Screening

Figure 3:
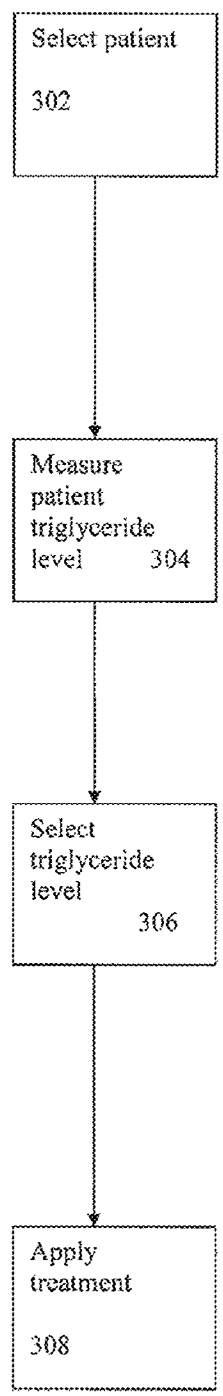
FIG. 3 is a flowchart of a method of screening patients for treatment, in accordance with an exemplary embodiment of the invention.

FIG. 3 is a method of selecting a patient (e.g., type 2 diabetic) for treatment according to the triglyceride level of the patient, in accordance with an exemplary embodiment of the invention.

At 302, a patient (e.g., diabetic) is selected for treatment, for example, as described with reference to box 202 in the section "EXEMPLARY METHOD OF TREATMENT", in accordance with an exemplary embodiment of the invention.

At 304, the triglyceride level of the patient is measured, for example, as described with reference to box 204 in the section "EXEMPLARY METHOD OF TREATMENT", in accordance with an exemplary embodiment of the invention.

At 306, the patient is selected for treatment according to the triglyceride level, in accordance with an exemplary embodiment of the invention.

In an exemplary embodiment of the invention, patients with a triglyceride level below a threshold value are selected for treatment. Optionally, the threshold value is empirically determined, for example, as described with reference to tables 7-13. Alternatively, the threshold value is calculated and/or estimated. One or more non-limiting examples for the threshold value include, 150 mg/dl, 100 mg/dl, 120 mg/dl, 140 mg/dl, 150 mg/dl, 160 mg/dl, 180 mg/dl, 200 mg/dl, or other smaller, intermediate or larger threshold values are used.

In an exemplary embodiment of the invention, the triglyceride level threshold is selected according to a desired and/or expected effect of treatment, such as using correlation tables. For example, as described with reference to tables 7-13, the expected effects of treatment in reducing HbA1c and/or weight loss after 3, 6 and/or 12 months are summarized according to varying triglyceride thresholds. Alternatively or additionally, the triglyceride level threshold is selected according to a sensitivity of treatment in achieving a desired and/or expected result. For example, the data may be analyzed and/or presented, in a manner such as for a threshold of X mg/dl, the probability of a reduction of Y % in HbA1c is Z %.

In an exemplary embodiment of the invention, the threshold value varies according to the patient characteristics. One or more non-limiting examples of factors affecting threshold values include, age, gender, race and/or genetic predisposition.

In an exemplary embodiment of the invention, the threshold value varies according to the treatment of the patient. Optionally, the threshold value varies according to the duration of the treatment. One or more non-limiting examples of factors affecting threshold values include, use of one or more triglyceride lowering agents, use of triglyceride lowering diet.

At 308, the patient is treated, for example, as described with reference to box 212 in the section "EXEMPLARY METHOD OF TREATMENT", in accordance with an exemplary embodiment of the invention.

Method of Adjusting Triglyceride Levels

Figure 4:
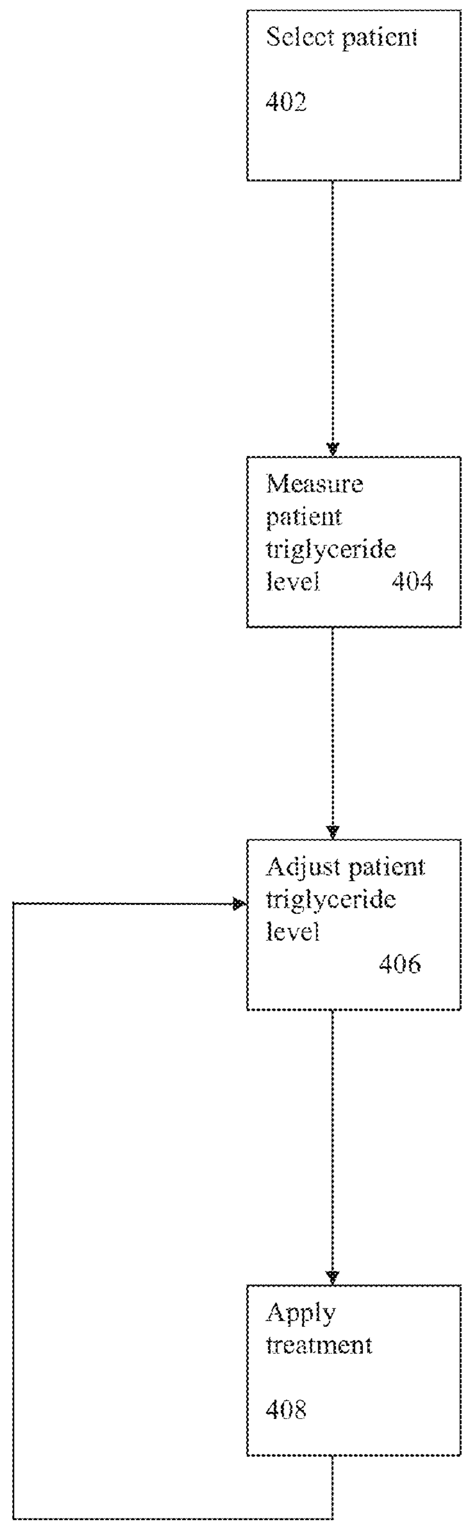
FIG. 4 is a flowchart of a method of adjusting triglyceride levels in patients as part of the treatment, in accordance with an exemplary embodiment of the invention.

FIG. 4 is a method of adjusting the triglyceride levels of a patient (e.g., type 2 diabetic) as part of medical treatment, in accordance with an exemplary embodiment of the invention.

At 402, a patient (e.g., diabetic) is selected for treatment, for example, as described with reference to box 202 in the section "EXEMPLARY METHOD OF TREATMENT", in accordance with an exemplary embodiment of the invention.

At 404, the triglyceride level of the patient is measured, for example, as described with reference to box 204 in the section "EXEMPLARY METHOD OF TREATMENT", in accordance with an exemplary embodiment of the invention.

At 406, the triglyceride level of the patient is adjusted, in accordance with an exemplary embodiment of the invention.

In an exemplary embodiment of the invention, the triglyceride level of the patient is reduced. Optionally, the triglyceride level is reduced to be below a threshold, for example, below 150 mg/dl, below 100 mg/dl, below 120 mg/dl, below 140 mg/dl, below 160 mg/dl, below 180 mg/dl, below 200 mg/dl, or other smaller, intermediate or larger thresholds are used. Some non-limiting examples of methods of selecting the threshold are described for example, with reference to box 306 in the section "METHOD OF SCREENING". Alternatively or additionally, the triglyceride level is reduced in a 'best effort' manner, for example, to be reduced as much as possible without trying to reach a target.

In an exemplary embodiment of the invention, the triglyceride levels are adjusted for those patients who have triglyceride levels above the threshold. Alternatively, the triglyceride levels are adjusted for all patients, regardless of their initial triglyceride level.

In an exemplary embodiment of the invention, the process of adjusting the triglyceride level is initiated before the start of treatment. Optionally, the triglyceride level is reduced to be below the target threshold before starting the treatment. Alternatively, the process of adjusting the triglyceride level continues throughout treatment to attempt to reach the target threshold. In some embodiments, the process of adjusting the triglyceride level is initiated after the start of treatment.

In an exemplary embodiment of the invention, the relatively low triglyceride levels are maintained for at least some of the treatment, for example, maintained to be below the threshold. Optionally, maintained triglyceride levels have been adjusted as part of treatment. Alternatively, maintained triglyceride levels are pre-existing levels in patients, for example, in patients with long term triglyceride lowering therapy prior to treatment (e.g., not adjusted as part of the treatment).

In an exemplary embodiment of the invention, patients undergo a medical examination for hypertriglyceridemia. Optionally, patients are evaluated for primary hypertriglyceridemia such as Familial Lipoprotein Lipase deficiency and/or Familial Hypertriglyceridemia, for example, by genetic history and/or genetic tests. Alternatively or additionally, patients are evaluated for secondary hypertriglyceridemia such as hypothyroidism and/or medications (e.g., corticosteroids, estrogen). In an exemplary embodiment of the invention, patients with primary and/or secondary causes of hypertriglyceridemia are treated more aggressively to lower the triglyceride levels (e.g., one or more triglyceride lowering drugs, relatively higher doses), and/or the cause of the relatively high triglycerides is treated (e.g., stopping medications such as steroids, treating hypothyroidism).

In some embodiments of the invention, patients with primary and/or secondary hypertriglyceridemia are included in treatment. Alternatively, patients are excluded from treatment. Optionally, patients are excluded until secondary causes are treated and/or controlled, and then included in the treatment.

In an exemplary embodiment of the invention, patients undergo measurements as part of the triglyceride level evaluation, such as blood tests. The plasma triglyceride level of the patients is measured by obtaining a venous sample from the patient that has fasted for at least 12 hours. Optionally, the level of very-low-density-lipoproteins (VLDL) in the patient's blood is measured. For example, a relatively high VLDL level (e.g., higher than 32 mg/dl) may be a marker for primary and/or secondary causes of hypertriglyceridemia. The primary and/or secondary causes can be treated as described in the previous paragraph. In some embodiments, VLDL levels can be used in addition to, or instead of triglyceride levels, for example, as described herein.

In some embodiments of the invention, a conservative approach is attempted for reducing the triglyceride level. Optionally, the process is attempted for 4-6 months, or other smaller, intermediate or larger ranges are used. One or more non-limiting examples of conservative measures include dietary changes and/or exercise. One or more non-limiting examples of dietary changes include reducing the consumption of fat and/or simple carbohydrates, increasing the consumption of omega-3 fatty acids, and/or reducing the consumption of alcohol.

In an exemplary embodiment of the invention, medical therapy is applied to reduce the triglyceride level. Optionally, the medical therapy is initiated after and/or in combination with the conservative approach.

Table 1 below illustrates one or more non-limiting examples of medical therapies to reduce triglyceride levels:

TABLE 1

| Drug Class | Mechanism of Action | Exemplary Drug | Exemplary Dosing |
|---|---|---|---|
| Statins (HMG CoA reductase inhibitors) | Inhibits cholesterol biosynthesis | Atorvastatin (Lipitor available from Pfizer) | 10-80 mg/day |
| Fibrates | Decreases lipolysis in adipose tissue | Bezafibrate | 400 mg/day |
| Niacin | Inhibits secretion of hepatic VLDL | Nicotinic acid | 1.5-3 g/day |
| Omega-3-fatty acids | Decreases SREBP-1 | N3-PUFA (Omacor) | 2-4 g/day |

At 408, the patient is treated, for example, as described with reference to box 212 in the section "EXEMPLARY METHOD OF TREATMENT", in accordance with an exemplary embodiment of the invention.

In an exemplary embodiment of the invention, treatment is started once the triglycerides have been sufficiently reduced, for example, below the threshold. Alternatively, treated is started after the patient has been stabilized at the triglyceride level (e.g., below the threshold), for example, one week after triglycerides have been reduced, or three months, or six months, or twelve months, or other smaller, intermediate or larger lengths of time are used.

Optionally, the triglyceride levels are adjusted after the start of treatment, for example, as in 406.

In some embodiments of the invention, the effects of the treatment are monitored, for example, the expected reduction in HbA1c. A non-limiting example of the expected effects of treatment is described with reference to FIG. 6C, which shows the change in magnitude of HbA1c as inversely correlated with the logarithm of the fasting triglyceride level. Optionally, the triglyceride level is adjusted as in 406 according to the treatment effects. For example, if the treatment results are below expectations (e.g., reduction in HbA1c is lower than as expected, such as predicted by FIG. 6C), additional attempts to relatively further reduce the triglyceride level can be attempted. Optionally, the treatment effects are used to decide how often to measure the triglyceride level, for example, measurements can be repeated (e.g., once every 120 days) if the treatment effects have stabilized, for example, HbA1c is not being further reduced.

In some embodiments of the invention, the triglyceride level threshold to which the triglycerides are attempted to be reduced below is identified per patient, for example, the threshold below which the treatment is relatively improved can differ in different patients. For example, in one patient, the treatment is relatively improved (e.g., relatively high reduction in HbA1c such as by 2.5%) below 200 mg/dl, while in another patient the treatment is relatively improved below 160 mg/dl. Optionally, once the threshold for the patient has been identified, the patient is stabilized on the current triglyceride lowering therapy.

Method of Choosing a Treatment

Figure 5:
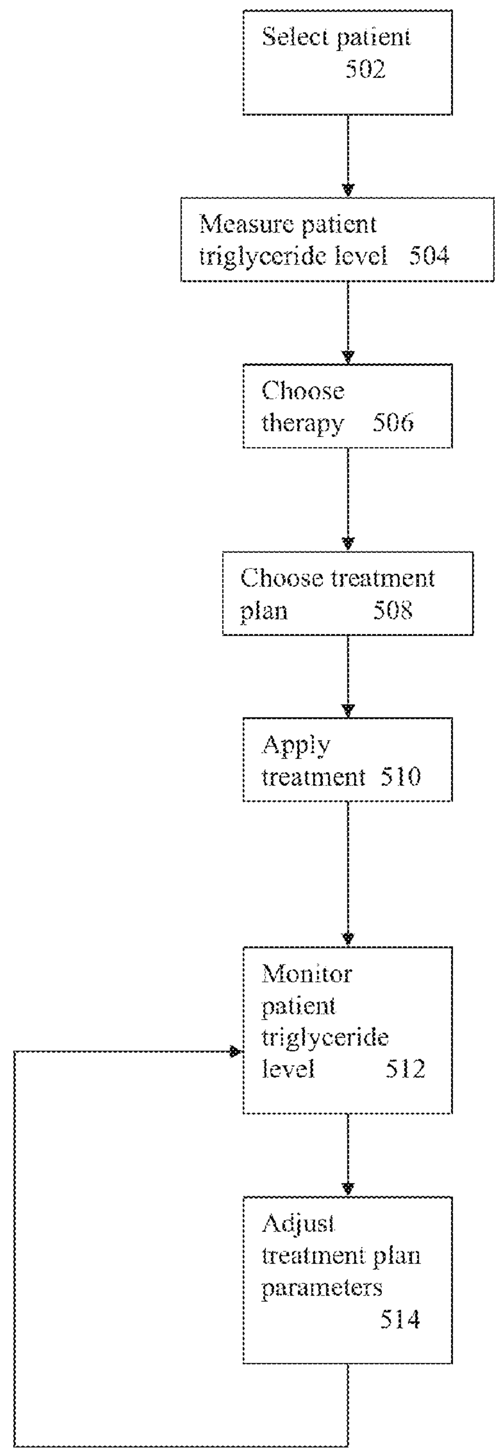
FIG. 5 is a flowchart of a method of adjusting treatment parameters for patients according to triglyceride levels, in accordance with an exemplary embodiment of the invention.

FIG. 5 is a method of selecting a treatment and/or treatment plan according to the triglyceride level of a patient (e.g., type 2 diabetic), in accordance with an exemplary embodiment of the invention. Optionally, the treatment and/or the treatment plan are adjusted according to the triglyceride level.

At 502, a diabetic patient is selected for example, as described with reference to box 202 in the section "EXEMPLARY METHOD OF TREATMENT", in accordance with an exemplary embodiment of the invention.

At 504, the triglyceride level of the patient is measured, for example, as described with reference to box 204 in the section "EXEMPLARY METHOD OF TREATMENT", in accordance with an exemplary embodiment of the invention.

At 506, treatment is selected, in accordance with an exemplary embodiment of the invention. Optionally, the treatment provided is abdominal stimulation, for example, gastric electrical stimulation by the gastric stimulatory device as described in the section "EXEMPLARY TREATMENT DEVICE".

At 508, the initial treatment plan (e.g., treatment parameters) is selected according to the triglyceride level as measured in 504, in accordance with an exemplary embodiment of the invention.

In an exemplary embodiment of the invention, the stimulation device is programmed with the triglyceride level measured as in 504. Optionally, the stimulation device is programmed manually, for example, by entering the triglyceride level (e.g., as measured by the blood test) into the programmer 106, and the programmer 106 transmits the data wirelessly to the stimulation device. In an exemplary embodiment of the invention, the stimulation device selects the treatment and/or treatment parameters according to the triglyceride levels, for example using the logic (e.g., using the table stored on the memory of the gastric stimulation device) as described in the section "EXEMPLARY TREATMENT DEVICE".

At 510, the treatment as in 506 is applied according to the selected treatment plan as in 508, in accordance with an exemplary embodiment of the invention.

Optionally, at 512, the triglyceride level of the patient is monitored, in accordance with an exemplary embodiment of the invention. Optionally, monitoring comprises one or more repeated triglyceride measurements (e.g., as in 504), for example, manual venous blood samples obtained once every week, once every two weeks month, once every month, once every three months once every six months, or other smaller, intermediate or larger time periods. Alternatively or additionally, monitoring comprises one or more repeated non-invasive measurements, optionally correlated with the triglyceride levels, for example, the levels of hepatic triglyceride content measured by magnetic resonance imaging (MRI). Alternatively or additionally, the effects of treatment are monitored, for example, as described in the section "METHOD OF ADJUSTING TRIGLYCERIDE LEVELS".

Optionally, at 514, the treatment parameters (e.g., as in 508) are adjusted, in accordance with an exemplary embodiment of the invention. Optionally, the treatment parameters are adjusted according to correlation values, for example, values stored in the memory of the gastric stimulation device, for example, as described in the section "EXEMPLARY TREATMENT DEVICE".

One or more examples of treatment parameters that are adjusted taking into account the triglyceride levels include:

Eating detection can be made more or less sensitive. A threshold can be set for the number of allowed meals.

Duration of therapy per meal can be adjusted, for example, 50 minutes, 70 minutes, 110 minutes, 120 minutes, 150 minutes, 180 minutes, or other smaller, intermediate and/or larger spans of time are used. The duration of therapy can be set according to the association between elevated triglycerides and decreased insulin secretion. Decreased insulin secretion can be associated with delayed metabolism. Based on the described associations, inventors hypothesize that to affect glucose uptake, treatment needs to be relatively longer.

Signal amplitude, for example, 10 mA, or 20 mA, or 5 mA, or 6 mA, or other smaller, intermediate or larger signal amplitudes are used.

Change in mixture and/or balance between signal types (e.g., combination and/or different composition of two or more signals), such as the GCM signal, Ruby signal, and/or other signals. Changes can be relative and/or absolute.

Treatment can be switched on or off based on the triglyceride level. One or more non-limiting examples include; treatment can be switched off to allow for another therapy to be used, shutting treatment off if the treatment has been found to be non-effective for certain triglyceride levels (e.g., to save power).

Optionally, treatment parameters are periodically and/or continuously adjusted in response to the monitored triglyceride level (e.g., as in 512), forming a feedback loop.

In some embodiments of the invention, the results of the treatment are compared against the expected effects of the treatment, for example, in reducing HbA1c and/or weight loss. Optionally, the expected treatment effects are determined by comparing the measured patient triglyceride level (e.g., as in 504) to triglyceride threshold tables and/or to the sensitivity table and/or graph, for example, as described with reference to box 306 in the section "METHOD OF SCREENING". Alternatively or additionally, the expected treatment effects are determined by a function, for example as described with reference to FIG. 6C, which shows the change in magnitude of HbA1c as inversely correlated with the logarithm of the fasting triglyceride level. Optionally, the treatment parameters as in 514 are adjusted with the goal of obtaining the expected treatment effect.

Potential Advantages

A potential advantage of selecting type 2 diabetic patients with relatively lower triglyceride levels for medical treatment, is relatively improving glycemic control (e.g., as manifested by reducing HbA1c levels) in the patients.

A potential advantage of using the threshold of 150 mg/dl (e.g., 140 mg/dl-150 mg/dl) for the triglyceride level is that this value for the threshold has been determined to be statistically significant by the inventors, for example, as described in the section "EXPERIMENTAL RESULTS". Another potential advantage of using the threshold of 150 mg/dl for the triglyceride level is that this value for the threshold is clinically significant, for example, patients having triglyceride levels above this threshold are considered having a risk factor as part of the clinical definition of the Metabolic Syndrome.

Support for the surprising association between the glycemic response to the treatment of type 2 diabetes and the plasma triglyceride level is provided, for example in the section "EXPERIMENTAL RESULTS".

A potential advantage of relatively lowering the plasma triglyceride levels in type 2 diabetic patients before and/or during the medical treatment, is relatively improving glycemic control (e.g., reducing HbA1c) in the patients.

A potential advantage of adjusting the treatment and/or treatment parameters according to the plasma triglyceride level, is relatively improving glycemic control (e.g., reducing HbA1c) in the patients.

A potential advantage of selecting patients with relatively lower triglyceride levels for medical treatment, is relatively improving weight loss in the patients. Optionally, the patients are type 2 diabetics.

A potential advantage of selecting patients with relatively higher blood pressures (e.g., systolic and/or diastolic) for medical treatment is relatively reducing the blood pressure in the patients, for example, as will be described below in the section "EXPERIMENTAL RESULTS".

A potential advantage of selecting type 2 diabetic patients with relatively lower triglyceride levels for medical treatment, is relatively improving insulin resistance in the patients, for example, as measured using the HOMA-IR index (as will be described below in the section "EXPERIMENTAL RESULTS").

A potential advantage of selecting type 2 diabetic patients with relatively lower triglyceride levels for medical treatment, is relatively improving insulin secretion in the patients, for example, as measured using the insulin/glucose ratio (as will be described below in the section "EXPERIMENTAL RESULTS").

A potential advantage of selecting type 2 diabetic patients with relatively lower triglyceride levels and relatively higher HbA1c levels (e.g., >=8.0%) for medical treatment, is relatively improving glycemic control (e.g., reducing HbA1c) in the patients.

Without being bound to theory, inventors believe that a potential advantage of the relatively lower plasma triglyceride level is direct potentiation of the glycemic effects of the gastric contractility modulation (e.g., by a device such as device 100 in FIG. 1). Such a result is surprising, as inventors are unaware of a similar effect with other antihyperglycemic agents or procedures. Without being bound to theory, another possibility is that triglycerides are markers for some other metabolic abnormality which occurs in patients with relatively higher triglyceride levels.

Without being bound to theory, inventors believe that a potential advantage of the relatively lower plasma triglyceride level is preventing and/or reducing lipotoxicity from playing a role in the pathogenesis and/or progression of type 2 diabetes, for example, by slowing the progression of type 2 diabetes as a result of reduced glucose levels. Increases in intracellular lipids (free fatty acids, triacylglycerol and/or triglyceride-rich lipoproteins) generate metabolic products such as diacylglycerols, long chain acyl-CoAs and/or ceramides. The excess in intracellular lipids in skeletal muscle, liver and/or heart muscle result in insulin resistance and/or altered organ function. There is strong evidence (e.g., in cell cultures and/or rodent models) that lipotoxicity is an important factor in increasing beta cell apoptosis and/or decreasing beta cell insulin secretion. Empirical evidence (e.g., as described in the section "EXPERIMENTAL RESULTS") illustrates that selectively stimulating patients with relatively low triglyceride levels results in relatively improved insulin resistance levels (e.g., as manifested by relatively reduced HOMA-IR levels). Inventors hypothesize that selectively stimulating patients with relatively low triglyceride levels extends the life of beta-cells. Inventors hypothesize that selectively stimulating patients with relatively low triglyceride levels increases insulin secretion by beta-cells.

Without being bound to theory, inventors believe that the potential advantage of the relatively lower plasma triglyceride level could be explained by an effect of chronic hypertriglyceridemia in blocking a presumed effect of gastric contractility modulation stimulation on the hypothalamic regulation of hepatic glucose production during feeding. For example, studies in rodents such as published by Lam et al in Nature Medicine 11:320-327, 2005 have identified that elevation of circulating fatty acids is recognized by the hypothalamus. The elevated levels are believed to trigger an autoregulatory effect on the liver to restrain hepatic glucose production. For example, experimental results support the hypothesis that circulating free fatty acids which are esterified in cells in the mediobasal hypothalamus activate hypothalamic ATP-dependent potassium channels. It is believed that activation of these channels causes signaling through selective centers in the brain stem to the descending fibers of the hepatic branch of the vagus nerve, potentially decreasing hepatic glucose production (e.g., neurally mediated autoregulation of the liver). Inventors hypothesize that abnormalities which interfere with the described pathway can lead to increased hepatic glucose production during exposure to lipids. Additionally, abnormalities of the hypothalamic ATP-dependent pathway can decrease the ability of central or peripheral insulin to decrease hepatic glucose production.

Experimental Results #1

Various embodiments and aspects of the present invention as delineated hereinabove and as claimed in the claims section below find experimental support in the following analysis of data obtained from several open label studies. The data below describes surprising findings discovered by the inventors. For example, that glycemic response (e.g., as manifested by relatively lower HbA1c levels) to chronic gastric electrical stimulation in patients with type 2 diabetes is inversely correlated with plasma triglycerides. For example, that patients with relatively lower plasma triglyceride levels treated with gastric electrical stimulation experienced; relatively greater weight loss, relatively greater reductions in systolic and/or diastolic blood pressures, relatively improved insulin resistance.

Methods

A total of 49 patients with type 2 diabetes were selected to participate in several almost identical open label studies of chronic gastric electrical stimulation with a non-excitatory signal which is triggered by eating detection (using the Tantalus device). The studies had similar design, inclusion, and exclusion criteria. Patients had inadequate glycemic control while on oral antidiabetic agents for 6 months or greater, and HbA1c values between 7% and 10.5%. Seventeen patients out of an analyzed sub-group of 40 patients (7 patients with a relatively low triglyceride level and 10 patients with a relatively high triglyceride level) were on statin therapy and one patient in the high triglyceride group was on fenofibrate. Patients were surgically implanted with the Tantalus gastric contractility modular device (e.g., as described in the section "EXEMPLARY TREATMENT DEVICE"). One to two weeks after surgery, the pulse generator was programmed to deliver the appropriate signal when food intake was detected by the fundal and/or antral electrodes. Food-mediated stimulation continued for 90 minutes after activation. In some embodiments, the device provides stimulation for up to 7 meals a day.

All 49 patients were followed for at least 6 months and a sub-group of 40 patients were followed for at least 12 months.

The baseline characteristics of the 40 patients whose data are presented herein were not statistically different, even when separated into two groups as defined by the fasting plasma triglyceride levels of <150 mg/dl and >=150 mg/dl. For the convenience of the reader, units of mg/dl and mmol/L are used herein interchangeably, for example 150 mg/dl is converted into 1.7 mmol/L (e.g., rounded off). There were no statistically significant differences in mean HbA1c, fasting plasma glucose (FPG), body weight, waist circumference, systolic or diastolic blood pressure, total cholesterol, LDL-cholesterol (low density lipoprotein), or HDL-cholesterol (high density lipoprotein) between the groups. Patient data is summarized in table 2 below:

TABLE 2

| | Fasting plasma Triglyceride (mmol/l) | N | Mean | SEM | P value |
|---|---|---|---|---|---|
| HbA1C (%) | <1.7 | 22 | 8.4 | 0.24 | Non |
| | >1.7 | 18 | 8.1 | 0.14 | Significant |
| FPG(mmol/l) | <1.7 | 20 | 10.3 | 0.37 | Non |
| | >1.7 | 17 | 9.9 | 0.37 | Significant |
| Weight (kg) | <1.7 | 22 | 106.8 | 4.51 | Non |
| | >1.7 | 18 | 115.1 | 5.49 | Significant |
| Waist (cm) | <1.7 | 18 | 106.8 | 4.51 | Non |
| | >1.7 | 13 | 115.1 | 5.49 | Significant |
| Systolic blood pressure | <1.7 | 22 | 141.7 | 4.1 | Non |
| (mm Hg) | >1.7 | 18 | 135.7 | 3.0 | Significant |
| Diastolic blood pressure | <1.7 | 22 | 85.3 | 2.9 | Non |
| (mm Hg) | >1.7 | 18 | 86.5 | 3.3 | Significant |
| Total Cholesterol | <1.7 | 22 | 4.61 | 0.23 | Non |
| (mmol/l) | >1.7 | 18 | 5.15 | 0.21 | Significant |
| LDL-Cholesterol | <1.7 | 21 | 2.91 | 0.22 | Non |
| (mmol/l) | >1.7 | 18 | 2.84 | 0.20 | Significant |
| HDL-Cholesterol | <1.7 | 21 | 1.18 | 0.05 | Non |
| (mmol/l) | >1.7 | 18 | 1.21 | 0.07 | Significant |

Measurements of glycemic control (fasting plasma glucose and/or HbA1c), and fasting lipids (triglycerides, total cholesterol, HDL-cholesterol and LDL-cholesterol) were carried out by the standard laboratory methods. Blood pressures were measured in the sitting position. The HOMA-IR level was calculated.

Results

Table 3 summarizes the baseline and change in HbA1c (e.g., glycemic control), weight and blood pressure for the 49 patients after 6 months of Gastric Contractility Modulation (GCM) treatment:

TABLE 3

| | HbA1C (%) | Body Weight (kg) | Systolic BP (mm Hg) | Diastolic BP (mm Hg) |
|---|---|---|---|---|
| Baseline | 8.4 ± 0.13 (49) | 109.3 ± 3.1 (49) | 138.3 ± 2.3 | 85.9 ± 1.7 |
| Change at 6 months | −1.0 ± 00.14** | −4.6 ± 0.68* | −19.7 ± 2.8** | −10.2 ± 1.5** |
| Triglyceride ≤ 1.7 mmol/1 | −1.4 ± 0.20 (27) | | | |
| Triglyceride > 1.7 mmol/1 | −0.5 ± 0.17 (22) | | | |

(* P < 0.01, ** P < 0.001, Number of patients in brackets)

The results show that from the mean baseline HbA1c of 8.4%, the patients had a mean decrease in HbA1c of 1.0±0.14 at 6 months of follow-up. The mean decrease in weight after 6 months was 4.6±0.68 kg, which was approximately 4.2% of the mean body weight.

The results for the mean decreases in systolic and/or diastolic blood pressures were surprising, as the decrease was relatively larger that what the inventors had expected to obtain as a result of the modest weight loss.

Since 40 of the 49 patients had complete HbA1c data for 3, 6 and 12 months of treatment, the detailed analyses presented will be confined to that population.

Analyses of the relationships between baseline parameters and the decreases in HbA1c indicated that the improvement in HbA1c was highly correlated with the baseline HbA1c level. However, an unexpected finding was that the change in HbA1c was inversely dependent on the fasting plasma triglyceride level (FTG).

The effect of GCM treatment on glycemic control was surprisingly different depending on baseline fasting plasma triglyceride levels. The changes in HbA1c after 6 months of GCM treatment (for the 49 patients) are summarized in table 3; patients with FTG<=1.7 mmol/l had a mean decrease in HbA1c of 1.4±0.20%, while patients with FTG>1.7 mmol/l had a mean decrease in HbA1c of 0.5±0.17%.

Figure 6A:
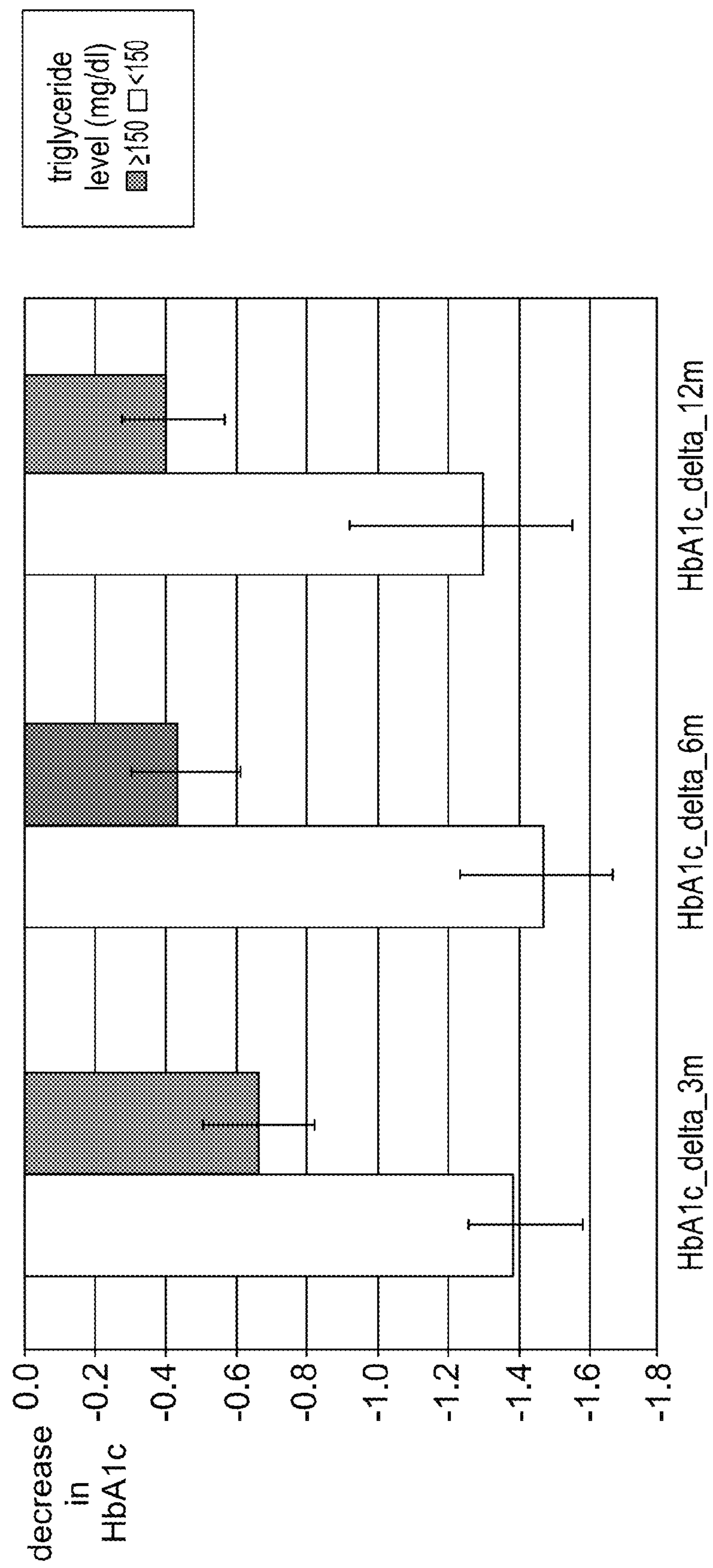
FIGS. 6A-6F are graphs of experimental results from a first experiment, useful in practicing some embodiments of the invention.

To further assess the potential relationships between the changes in HbA1c and FTG, data from 40 patients who had been treated for more than one year and had complete data sets at 3, 6, and 12 months were analyzed in detail. FIG. 6A is graph showing the mean decrease in HbA1c after 3, 6 and 12 months of treatment, separated into the patient subgroups of fasting plasma triglycerides≤150 mg/dl (relatively low TG) and patients with fasting plasma triglycerides>150 mg/dl (relatively high TG). Table 4 presents the results (e.g., as in FIG. 6A) of the effect of FTG on the decrease in HbA1c (% magnitude reduction) at 3, 6, and 12 months, in tabular format for the convenience of the reader.

TABLE 4

| Number of Patients | Fasting Triglyceride Levels | Change at 3 Months | Change at 6 Months | Change at 12 Months |
|---|---|---|---|---|
| 22 | FTG ≤ 1.7 mmol/1 | −1.39 ± 0.20 | −1.48 ± 0.20 | −1.32 ± 0.26 |
| 18 | FTG > 1.7 mmol/1 | −0.66 ± 0.16 | −0.44 ± 0.18 | −0.42 ± 0.16 |

The results were surprising, as the decrease in HbA1c in those with relatively low TG averaged between 1.4% and 1.3% at 3, 6 and 12 months. In contrast, the decrease in HbA1c was 0.7% at 3 months and decreased to 0.4% at 12 months in those with relatively high TG.

Figure 6B:
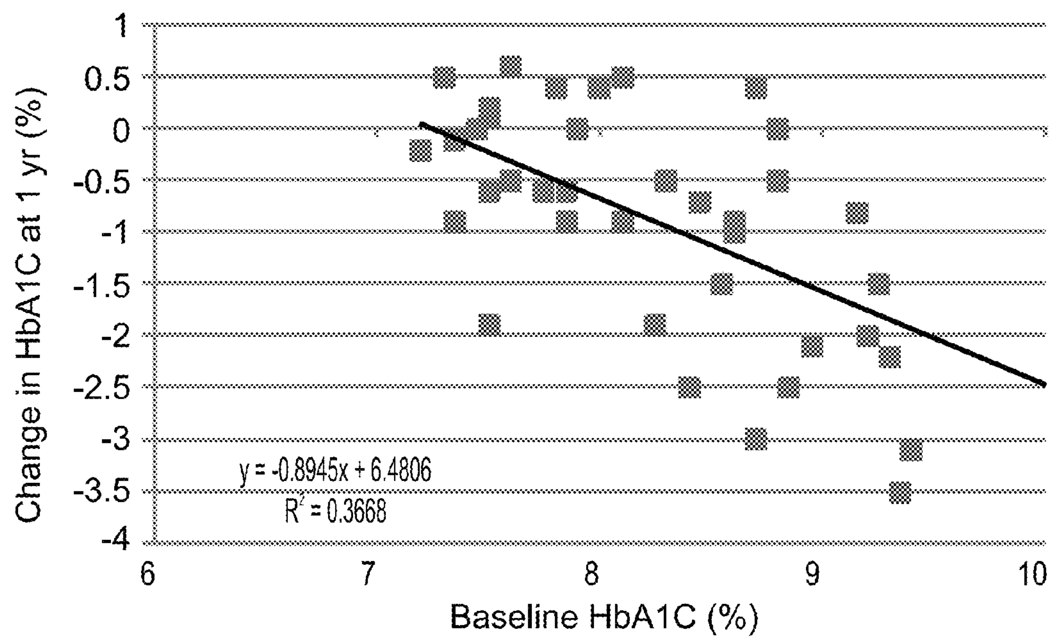

FIG. 6B is a graph showing that the change in magnitude of the HbA1c in the 40 patients treated for at least 1 year by gastric electrical stimulation was highly linearly correlated with the baseline HbA1c ($R=0.606$, $p<0.001$).

Table 5 illustrates that the predictability of the magnitude of HbA1c response to GCM stimulation in the low and high TG groups is significant in those patients with baseline HbA1C>=8%. Surprisingly, the greatest improvement in glycemic control with GCM stimulation is seen in the sub-group of patients with low TG and a baseline HbA1c of 8.0% or greater.

TABLE 5

| | Baseline HbA1c < 8.0 % | Baseline HbA1c 8.0-9.0 % | Baseline HbA1c > 9.0 % |
|---|---|---|---|
| Low TG | −0.3 ± 0.28 (8) | −1.6 ± 0.34 (9) | −2.4 ± 0.40 (5) |
| High TG | −0.3 ± 0.17 (9) | −0.3 ± 0.26 (7) | −1.4 ± 0.60 (2) |

(Number of patients in parentheses)

Figure 6C:
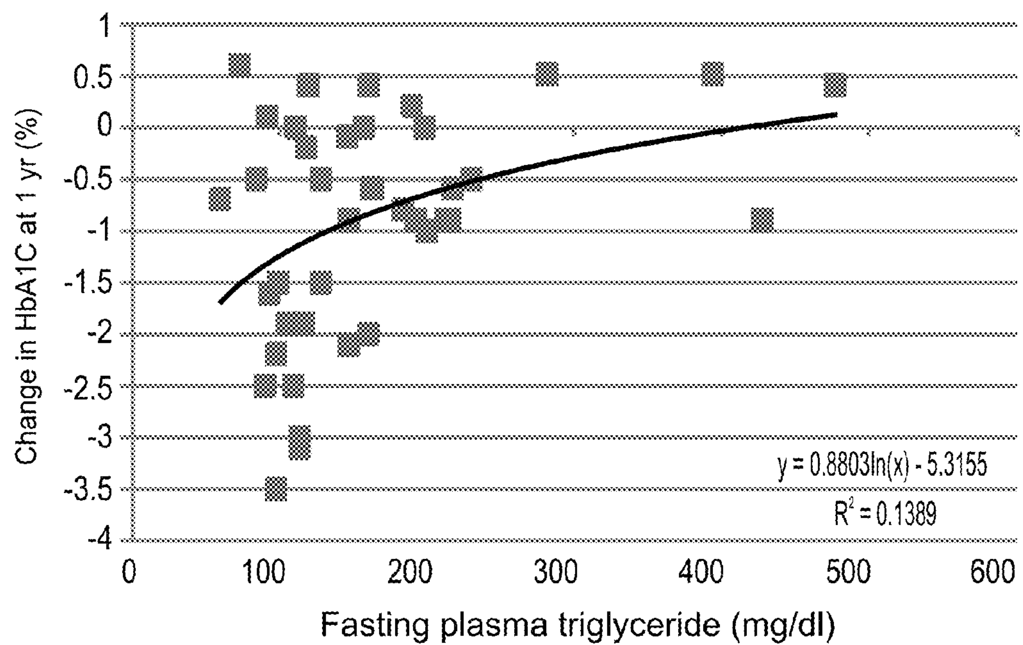

FIG. 6C is a graph showing that the change in the magnitude of HbA1c in the 40 patients treated for at least 1 year by gastric electrical stimulation was inversely correlated with the logarithm of FTG ($R=0.373$, $p<0.05$).

Figure 6D:
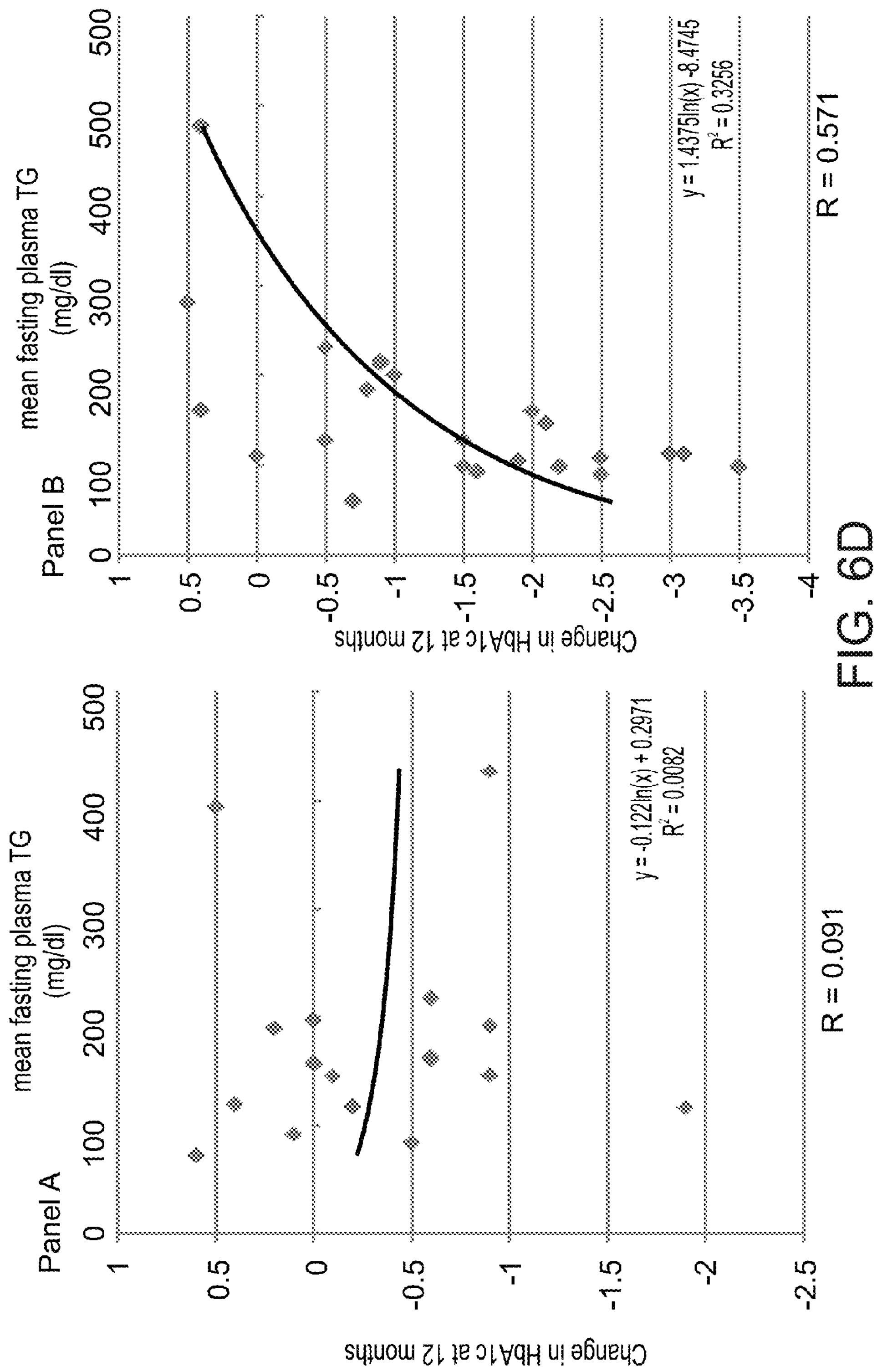

FIG. 6D presents the data of FIG. 6C according to baseline HbA1c levels. The left side of FIG. 6D is a graph of patients having a baseline HbA1c level of 7.0-7.9% as a function of the decrease in HbA1c after 12 months of GCM stimulation.

There is relatively little relationship between the fasting plasma triglycerides and the decrease in HbA1c after 1 year of GCM treatment. The right side of FIG. 6D is a graph of patients having a baseline HbA1c of 8.0-10.3%. There is a striking inverse relationship between the logarithm of the fasting plasma triglyceride level and the decrease in HbA1c after 12 months of GCM stimulation. The surprising results show that the greatest improvement in glycemic control with GCM stimulation is seen in patients with relatively low TG and a baseline HbA1C of 8.0% or greater.

Figure 6E:
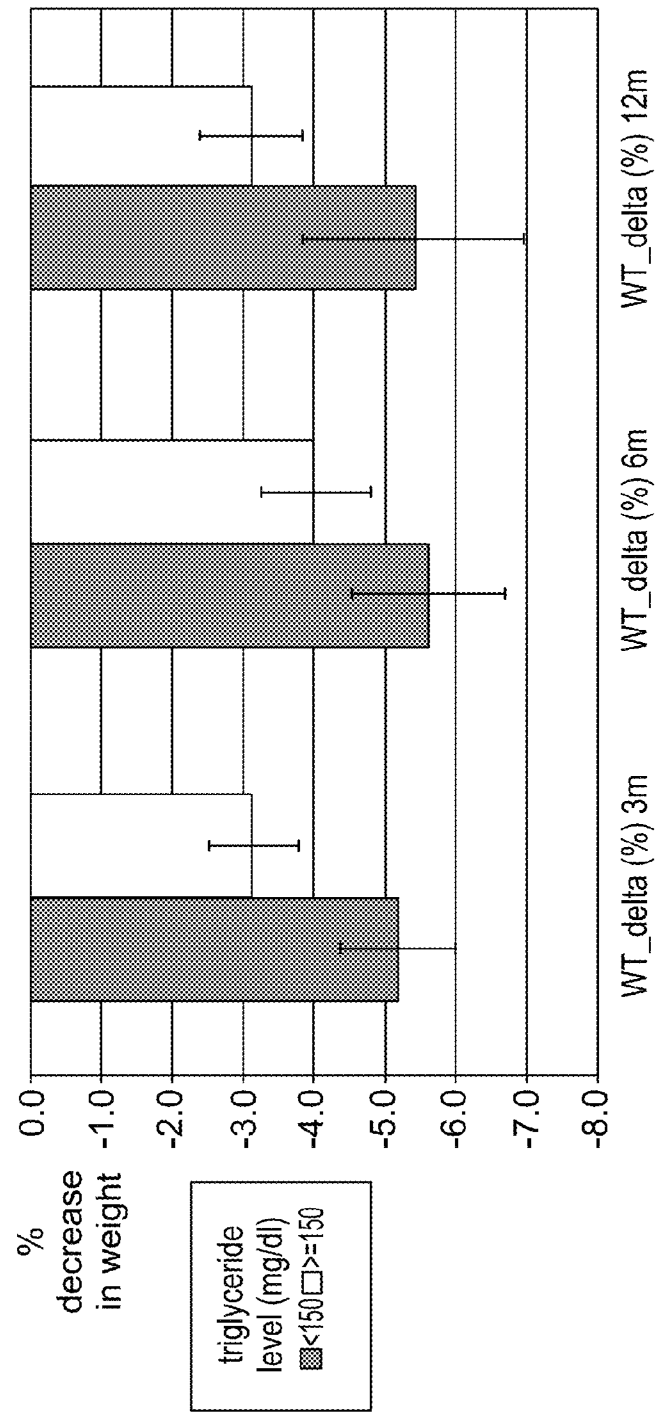

GCM stimulation caused a modest weight loss as well as an improvement in glycemic control. FIG. 6E shows that the patients with relatively low FTG had about a 2 kg greater weight loss as compared to patients with relatively high FTG.

Figure 6F:
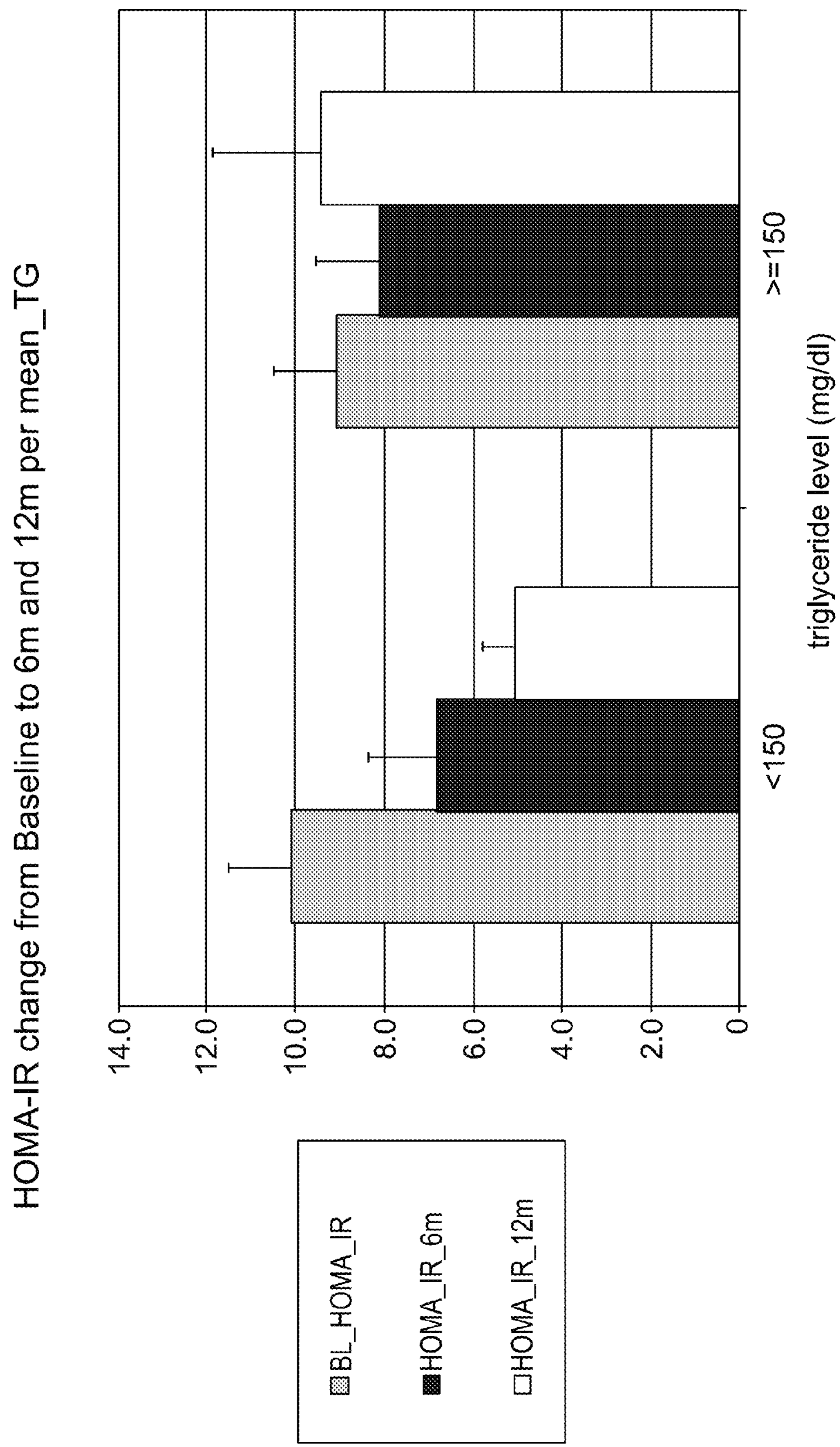

FIG. 6F is a graph of the mean HOMA-IR at baseline, 6 months and 12 months for the patients with relatively low TG and relatively high TG. Surprisingly, the analysis of the results indicates that the HOMA-IR change during therapy was associated with the relative TG level. Patients with relatively low FTG had a statistically significant decrease in HOMA-IR as compared to patients with relatively high FTG. Surprisingly, relatively higher improvements in HOMA-IR were seen at 6 and/or 12 months in the low TG patients.

Table 6 summarizes the metabolic and lipid parameters after 6 months of GCM treatment. The parameters are separated by fasting plasma triglycerides less than vs. greater than 1.7 mmol/l.

TABLE 6

| | Fasting Triglyceride (mmol/1) | N | Mean | SEM | P value |
|---|---|---|---|---|---|
| FPG (mmol/1) | <1.7 | 22 | 7.93 | 0.37 | 0.18 |
| | >1.7 | 18 | 8.72 | 0.45 | |
| | All | 40 | 8.28 | 0.29 | |
| Waist (cm) | <1.7 | 16 | 114.0 | 3.29 | 0.06 |
| | >1.7 | 13 | 123.2 | 3.36 | |
| | All | 29 | 118.1 | 2.42 | |
| Systolic blood pressure (mm Hg) | <1.7 | 22 | 124.9 | 3.14 | 0.30 |
| | >1.7 | 18 | 131.4 | 5.59 | |
| | All | 40 | 127.9 | 3.05 | |
| Diastolic blood pressure (mm Hg) | <1.7 | 22 | 76.2 | 2.40 | 0.16 |
| | >1.7 | 18 | 81.9 | 3.30 | |
| | All | 40 | 78.8 | 2.01 | |
| Total cholesterol (mmol/1) | <1.7 | 18 | 4.47 | 0.30 | 0.49 |
| | >1.7 | 15 | 4.75 | 0.22 | |
| | All | 33 | 4.60 | 0.20 | |
| LDL-cholesterol (mmol/1) | <1.7 | 18 | 2.74 | 0.25 | 0.41 |
| | >1.7 | 14 | 2.44 | 0.23 | |
| | All | 32 | 2.61 | 0.17 | |
| HDL-cholesterol (mmol/1) | <1.7 | 18 | 44.88 | 0.07 | 0.90 |
| | >1.7 | 15 | 45.33 | 0.05 | |
| | All | 33 | 45.08 | 0.04 | |
| Plasma triglyceride (mmol/1) | <1.7 | 18 | 1.16 | 0.07 | 0.001 |
| | >1.7 | 15 | 2.52 | 0.40 | |
| | All | 33 | 1.78 | 0.22 | |

Additional Data Analysis

Inventors analyzed the data of the 40 patients for the decrease in HbA1c and/or the decrease in weight according to triglyceride threshold values of 100 mg/dl, 120 mg/dl, 140 mg/dl, 150 mg/dl, 160 mg/dl, 180 mg/dl and/or 200 mg/dl. For each threshold, changes in HbA1c and/or weight were analyzed after 3, 6 and/or 12 months of gastric contractility modulation treatment. The results are presented in tables 7-13.

For this patient group, the threshold of 150 mg/dl was selected due to relatively higher statistical significance and/or relatively equal distribution of patients between the two analysis groups. Furthermore, another reason for selection of this threshold is that 150 mg/dl can be clinically significant, for example, the triglyceride level above 150 mg/dl is considered a risk factor in the clinical definition of Metabolic Syndrome.

It should be noted, that although 150 mg/dl was selected as a threshold for this patient group, another threshold may be determined for other patients groups (e.g., having different characteristics), for example, by analyzing the data as in tables 7-13. Generally, as relatively lower TG thresholds are selected, patients having the relatively lower TG levels have relatively improved reductions in HbA1c and/or weight. Generally, as relatively higher TG thresholds are selected, patients having the relatively higher TG levels have relatively reduced improvements in HbA1c and/or weight. Non-limiting examples of the use of the tables include; planning aggressive treatment for patients, and/or estimating the expected success of treatment according to patient TG levels. Generally as relatively lower and/or relatively higher TG thresholds are selected, results become relatively less reliable (e.g., as manifested by the 'P-value') for these other subgroups, for example, due to the relatively smaller number of patients and/or relatively larger differences in number of patients between treatment groups. In some embodiments, additional patient data is collected from relatively larger number of patients to relatively improve the reliability of the results.

TABLE 7

| Triglyceride threshold of 100 mg/dl | | | | | |
|---|---|---|---|---|---|
| | BL_TG_2groups100 | N | Mean | Std. Deviation | P-Value |
| HbA1c_Delta_3m | <=100 | 9 | −1.6 | .9 | |
| | >100 | 31 | −.9 | .8 | 0.05 |
| | Total | 40 | −1.1 | .9 | |
| HbA1c_Delta_6m | <=100 | 9 | −1.7 | 1.0 | |
| | >100 | 31 | −.8 | .9 | 0.009 |
| | Total | 40 | −1.0 | 1.0 | |
| HbA1c_Delta_12m | <=100 | 9 | −1.3 | 1.3 | |
| | >100 | 31 | −.8 | 1.0 | NS |
| | Total | 40 | −.9 | 1.1 | |
| Weight_Delta_3m | <=100 | 9 | −5.8 | 4.0 | |
| | >100 | 31 | −3.8 | 3.3 | NS |
| | Total | 40 | −4.3 | 3.5 | |
| Weight_Delta_6m | <=100 | 9 | −6.3 | 5.8 | |
| | >100 | 31 | −4.4 | 3.8 | NS |
| | Total | 40 | −4.9 | 4.3 | |
| Weight_Delta_12m | <=100 | 8 | −5.8 | 8.4 | |
| | >100 | 31 | −3.9 | 4.9 | NS |
| | Total | 39 | −4.3 | 5.7 | |

TABLE 8

| Triglyceride threshold of 120 mg/dl | | | | | |
|---|---|---|---|---|---|
| | BL_TG_2groups120 | N | Mean | Std. Deviation | P-Value |
| HbA1c_Delta_3m | <=120 | 14 | −1.6 | 1.1 | |
| | >120 | 26 | −.8 | .6 | 0.005 |
| | Total | 40 | −1.1 | .9 | |

TABLE 8-continued

| Triglyceride threshold of 120 mg/dl | | | | | |
|---|---|---|---|---|---|
| | BL_TG_2groups120 | N | Mean | Std. Deviation | P-Value |
| HbA1c_Delta_6m | <=120 | 14 | −1.7 | 1.0 | |
| | >120 | 26 | −.7 | .8 | 0.001 |
| | Total | 40 | −1.0 | 1.0 | |
| HbA1c_Delta_12m | <=120 | 14 | −1.5 | 1.4 | |
| | >120 | 26 | −.6 | .8 | 0.02 |
| | Total | 40 | −.9 | 1.1 | |
| Weight_Delta_3m | <=120 | 14 | −6.3 | 3.9 | |
| | >120 | 26 | −3.2 | 2.7 | 0.005 |
| | Total | 40 | −4.3 | 3.5 | |
| Weight_Delta_6m | <=120 | 14 | −6.6 | 5.0 | |
| | >120 | 26 | −4.0 | 3.7 | NS |
| | Total | 40 | −4.9 | 4.3 | |
| Weight_Delta_12m | <=120 | 13 | −6.3 | 7.8 | |
| | >120 | 26 | −3.3 | 4.2 | NS |
| | Total | 39 | −4.3 | 5.7 | |

TABLE 9

| Triglyceride threshold of 140 mg/dl | | | | | |
|---|---|---|---|---|---|
| | BL_TG_2groups140 | N | Mean | Std. Deviation | P-Value |
| HbA1c_Delta_3m | <=140 | 18 | −1.5 | 1.0 | |
| | >140 | 22 | −.7 | .6 | 0.006 |
| | Total | 40 | −1.1 | .9 | |
| HbA1c_Delta_6m | <=140 | 18 | −1.5 | 1.0 | |
| | >140 | 22 | −.6 | .8 | 0.002 |
| | Total | 40 | −1.0 | 1.0 | |
| HbA1c_Delta_12m | <=140 | 18 | −1.3 | 1.3 | |
| | >140 | 22 | −.6 | .8 | 0.025 |
| | Total | 40 | −.9 | 1.1 | |
| Weight_Delta_3m | <=140 | 18 | −5.3 | 4.1 | |
| | >140 | 22 | −3.4 | 2.7 | NS |
| | Total | 40 | −4.3 | 3.5 | |
| Weight_Delta_6m | <=140 | 18 | −5.5 | 5.0 | |
| | >140 | 22 | −4.3 | 3.8 | NS |
| | Total | 40 | −4.9 | 4.3 | |
| Weight_Delta_12m | <=140 | 17 | −5.0 | 7.2 | |
| | >140 | 22 | −3.8 | 4.3 | NS |
| | Total | 39 | −4.3 | 5.7 | |

Table 10

| Triglyceride threshold of 150 mg/dl | | | | | | |
|---|---|---|---|---|---|---|
| | TG_Avg_2groups150 | N | Mean | Std. Deviation | Std. Error of Mean | ANOVA P-Value |
| HbA1cDelta_3m | <150 | 22 | −1.4 | 0.92 | 0.20 | 0.008 |
| | >=150 | 18 | −0.7 | 0.67 | 0.16 | |
| | Total | 40 | −1.1 | 0.88 | 0.14 | |
| HbA1cDelta_6m | <150 | 22 | −1.5 | 0.92 | 0.20 | <0.0001 |
| | >=150 | 18 | −0.4 | 0.75 | 0.18 | |
| | Total | 40 | −1.0 | 0.99 | 0.16 | |
| HbA1cDelta_12m | <150 | 22 | −1.3 | 1.20 | 0.26 | 0.008 |
| | >=150 | 18 | −0.4 | 0.67 | 0.16 | |
| | Total | 40 | −0.9 | 1.08 | 0.17 | |
| Weight_Delta_3m | <150 | 22 | −5.2 | 3.84 | 0.82 | 0.06 |
| | >=150 | 18 | −3.1 | 2.68 | 0.63 | |
| | Total | 40 | −4.3 | 3.48 | 0.55 | |
| Weight_Delta_6m | <150 | 22 | −5.6 | 5.00 | 1.07 | |
| | >=150 | 18 | −4.0 | 3.29 | 0.77 | 0.25 |
| | Total | 40 | −4.9 | 4.34 | 0.69 | |
| Weight_Delta_12m | <150 | 21 | −5.4 | 7.13 | 1.56 | |
| | >=150 | 18 | −3.1 | 3.03 | 0.71 | 0.20 |
| | Total | 39 | −4.3 | 5.68 | 0.91 | |

TABLE 11

| Triglyceride threshold of 160 mg/dl | | | | | |
|---|---|---|---|---|---|
| | BL_TG_2groups160 | N | Mean | Std. Deviation | P-Value |
| HbA1c_Delta_3m | <=160 | 22 | −1.3 | 1.0 | |
| | >160 | 18 | −.7 | .6 | 0.02 |
| | Total | 40 | −1.1 | .9 | |
| HbA1c_Delta_6m | <=160 | 22 | −1.5 | .9 | |
| | >160 | 18 | −.4 | .7 | <0.0001 |
| | Total | 40 | −1.0 | 1.0 | |
| HbA1c_Delta_12m | <=160 | 22 | −1.3 | 1.2 | |
| | >160 | 18 | −.4 | .7 | 0.005 |
| | Total | 40 | −.9 | 1.1 | |
| Weight_Delta_3m | <=160 | 22 | −5.1 | 3.9 | |
| | >160 | 18 | −3.3 | 2.7 | NS |
| | Total | 40 | −4.3 | 3.5 | |
| Weight_Delta_6m | <=160 | 22 | −6.0 | 4.9 | |
| | >160 | 18 | −3.5 | 3.1 | NS |
| | Total | 40 | −4.9 | 4.3 | |
| Weight_Delta_12m | <=160 | 21 | −5.5 | 7.1 | |
| | >160 | 18 | −2.9 | 3.0 | NS |
| | Total | 39 | −4.3 | 5.7 | |

TABLE 12

| Triglyceride threshold of 180 mg/dl | | | | | |
|---|---|---|---|---|---|
| | BL_TG_2g roups180 | N | Mean | Std. Deviation | P-Value |
| HbA1c_Delta_3m | <=180 | 27 | −1.2 | .9434 | NS |
| | >180 | 13 | −.8 | .7 | |
| | Total | 40 | −1.1 | .9 | |
| HbA1c_Delta_6m | <=180 | 27 | −1.2 | 1.0 | NS |
| | >180 | 13 | −.6 | .8 | |
| | Total | 40 | −1.0 | 1.0 | |
| HbA1c_Delta_12m | <=180 | 27 | −1.2 | 1.1 | 0.005 |
| | >180 | 13 | −.2 | .6 | |
| | Total | 40 | −.9 | 1.1 | |
| Weight_Delta_3m | <=180 | 27 | −5.0 | 3.6 | NS |
| | >180 | 13 | −2.8 | 2.8 | |
| | Total | 40 | −4.3 | 3.5 | |
| Weight_Delta_6m | <=180 | 27 | −5.7 | 4.7 | NS |
| | >180 | 13 | −3.2 | 3.0 | |
| | Total | 40 | −4.9 | 4.3 | |
| Weight_Delta_12m | <=180 | 26 | −5.0 | 6.6 | NS |
| | >180 | 13 | −2.9 | 3.0 | |
| | Total | 39 | −4.3 | 5.7 | |

TABLE 13

| Triglyceride threshold of 200 mg/dl | | | | | |
|---|---|---|---|---|---|
| | BL_TG_2g roups200 | N | Mean | Std. Deviation | P-Value |
| HbA1c_Delta_3m | <=200 | 30 | −1.2 | .9 | |
| | >200 | 10 | −.8 | .7 | NS |
| | Total | 40 | −1.1 | .9 | |
| HbA1c_Delta_6m | <=200 | 30 | −1.1 | 1.0 | |
| | >200 | 10 | −.6 | .9 | NS |
| | Total | 40 | −1.0 | 1.0 | |
| HbA1c_Delta_12m | <=200 | 30 | −1.1 | 1.1 | |
| | >200 | 10 | −.4 | .6 | NS |
| | Total | 40 | −.9 | 1.1 | |
| Weight_Delta_3m | <=200 | 30 | −4.7 | 3.6 | |
| | >200 | 10 | −2.9 | 2.9 | NS |
| | Total | 40 | −4.3 | 3.5 | |
| Weight_Delta_6m | <=200 | 30 | −5.4 | 4.7 | |
| | >200 | 10 | −3.4 | 2.8 | NS |
| | Total | 40 | −4.9 | 4.3 | |
| Weight_Delta_12m | <=200 | 29 | −4.8 | 6.3 | |
| | >200 | 10 | −2.9 | 2.8 | NS |
| | Total | 39 | −4.3 | 5.7 | |

Experimental Results #2

Purpose:

Inventors performed a single center study (in addition to the previously described study) to evaluate the relationship between plasma triglyceride levels and effects of GCM treatment on the metabolic response to a meal tolerance test. The study was also conducted to confirm the effect of GCM on HbA1c levels.

Method:

9 patients with type 2 diabetes initiated treatment with GCM entered the study. 8 patients completed the study. Of the 8 patients who completed the meal tolerance test with hormone measurements at baseline and after 26 weeks of GCM, 4 had fasting triglyceride levels below 1.7 mmol/l and 4 had levels above 1.7 mmol/1.

Patients underwent a meal tolerance test at baseline and again after 25 weeks of treatment. Glucose, insulin, glucagon and levels were measured at baseline and again at 25 weeks for comparison. Plasma triglyceride levels were measured at baseline. Weight was measured at baseline and at 25 weeks.

Results:

As shown in Table 14, the changes in HbA1c and weight were not significant when all patients were considered together.

TABLE 14

| summary data for all 9 patients: | | |
|---|---|---|
| Baseline HbA1c | 7.94% | |
| 25 week HbA1c | 7.17% | p = 0.079 |
| Baseline weight | 114.3 kg | |
| 25week weight | 110.7 kg | p = 0.48 |

As shown below in table 15, when patients were analyzed according to a triglyceride threshold of 1.7 mmol/l (150 mg/dl), patients with TG<1.7 mmol/l had statistically significant (p<0.05) reductions in HbA1c and weight.

TABLE 15

| analysis according to TG threshold | | |
|---|---|---|
| Triglycerides < 1.7 mmol/l (150 mg/dl) N = 5 | | |
| Baseline HbA1c | 7.78 % | |
| 25 week HbA1c | 6.56 % | p = 0.021 |
| Baseline weight | 105.6 kg | |
| 25 week weight | 100.2 kg | p = 0.035 |
| Triglycerides > 1.7 mmol/l (150 mg/dl) | | |
| Baseline HbA1c | 8.15 % | |
| 25 week HbA1c | 7.93 % | p = 0.66 |
| Baseline weight | 125.3 kg | |
| 25 week weight | 123.8 kg | p = 0.39 |

As shown below in table 16, overall, patients treated with GCM appeared to display; decrease in glucose levels, increase in insulin, increase in insulin/glucose, and/or a decrease in glucose. The changes in glucose, insulin and glucagon were used as indicators that the endocrine system of the patients behaves as expected for this group of patients.

The increase in insulin/glucose ratio>0 is due to more insulin and/or less glucose. The result supports the hypothesis that glucose levels were reduced without increasing release of insulin, supporting the hypothesis that the treatment improved insulin resistance in the patients. Alternatively or additionally, it is hypothesized that the patients were able to obtain additional insulin when needed (e.g., immediately in response to eating), supporting the hypothesis that treatment helped improve secretion of endogenous insulin in patients.

TABLE 16

| Data analyses of 8 meal tolerance responses: treatment response (25 week) compared to baseline response | | |
|---|---|---|
| Glucose | Decrease 7.35 % | p = 0.0003 |
| Insulin | Increase 16.5 % | p = 0.015 |
| Insulin/glucose | Increase 26.9 % | p = 0.0024 |
| Glucagon | Decrease 10 % | p = 0.000025 |

As shown below in table 17, patients with TG<=1.7 mmol/l had statistically significant changes (p<0.05) in insulin/glucose as compared to baseline.

TABLE 17

(baseline was combined for all 8 pateints; low TG = 4; high TG = 4)

| Patient group | Glucose | Insulin | Insulin/glucose | Glucagon |
|---|---|---|---|---|
| Baseline to 25 weeks: TG < 1.7 mmol/1 | 0.07 | 0.12 | 0.004 | 0.005 |
| Baseline to 25 weeks: TG > 1.7 mmol/1 | 0.89 | 0.66 | 0.52 | 0.45 |

Figure 7A:
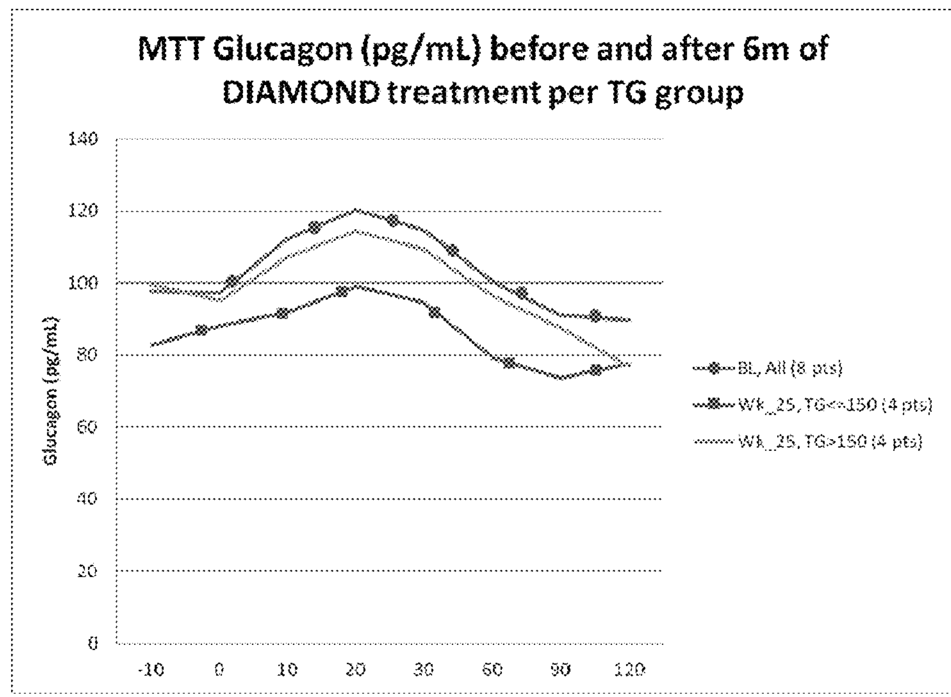
FIGS. 7A-7B are graphs of experimental results from a second experiment.
Figure 7B:
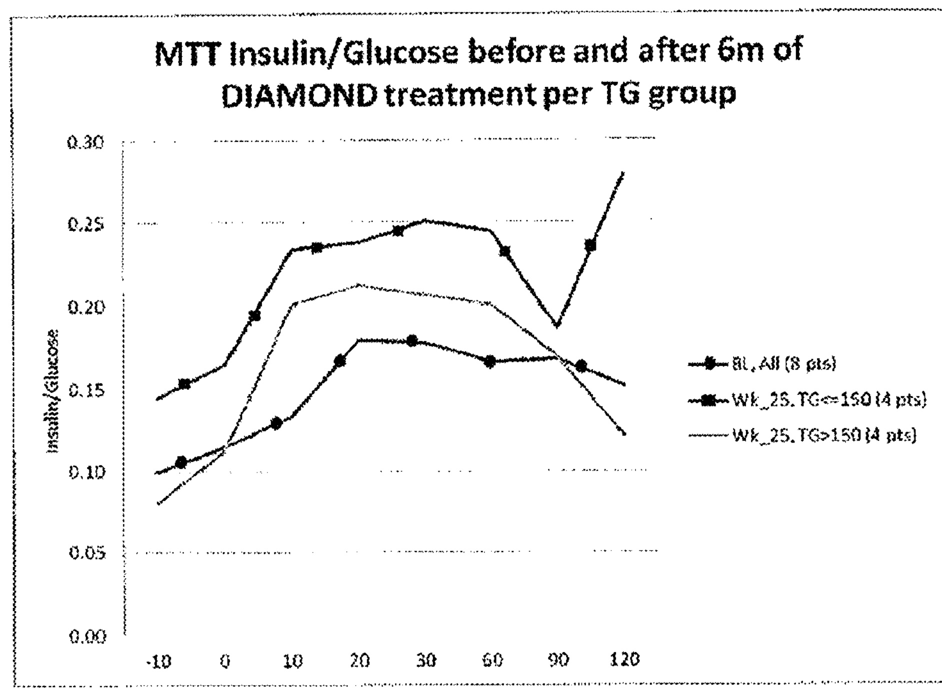

For the convenience of the reader, FIGS. 7A-7B present some of the data in graphical format. FIG. 7A is a graph of glucagon levels before and after 6 months of GCM treatment, in all patients, and broken down according to the TG threshold of 150 mg/dl. FIG. 7B is a graph of insulin/glucose before and after 6 months of GCM treatment, for all patients and broken down according to the TG threshold of 150 mg/dl.

CONCLUSION

The experimental results provide support to the hypothesis that treatment with abdominal and/or gastric stimulation in type 2 diabetic patients with TG<=150 mg/dl at least in part helps to reduce HbA1c levels and/or weight as compared to a pre-treatment baseline.

The experimental results also provide support to the hypothesis that treatment with abdominal and/or gastric stimulation in type 2 diabetic patients with TG<=150 mg/dl at least partially helps to increase endogenous insulin secretion (per unit of glucose) as compared to a pre-treatment baseline.

It is expected that during the life of a patent maturing from this application many relevant methods of improving glycemic control will be developed and the scope of the term glycemic control is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

General

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a diabetic patient comprising:

measuring a triglyceride level and HbA1c level in said diabetic patient;

selecting said patient for treatment according to said triglyceride level being below a threshold, and HbA1c level being above a threshold; and applying said treatment to said selected patient, said treatment comprising at least one of intra-abdominal and gastric electrical stimulation.

2. A method according to claim 1, wherein said applying comprises applying said treatment to reduce said HbA1c level by at least 1.0% after 3 months of said treatment.

3. A method according to claim 1, wherein said diabetic patient is a type 2 diabetic patient.

4. A method according to claim 1, wherein said triglyceride threshold comprises a triglyceride level<=150 mg/dl.

5. A method according to claim 1, wherein said triglyceride threshold comprises a triglyceride level<=120 mg/dl.

6. A method according to claim 1, wherein said triglyceride threshold comprises a triglyceride level<=180 mg/dl.

7. A method according to claim 1, wherein said applying comprises applying said diabetes treatment according to a function of triglyceride levels and expected effects of treatment.

8. A method according to claim 1, wherein said triglyceride level comprises a fasting plasma triglyceride level.

9. A method according to claim 1, further comprising:
reducing said triglyceride level in said patient during at least one of before and during said treatment.

10. A method according to claim 9, wherein said reducing comprises administering at least one drug.

11. A method according to claim 10, wherein said at least one drug comprises selecting from the group consisting of: statin, fibrate, niacin.

12. A method according to claim 9, wherein said reducing comprises at least one dietary change.

13. A method according to claim 12, wherein said at least one dietary change comprises selecting from the group consisting of: reducing fat, reducing carbohydrates, increasing omega-3 fatty acids, reducing alcohol.

14. A method according to claim 1, further comprising:
monitoring changes in said triglyceride level during at least one of said treatment and during said treatment; and
at least one of adjusting said treatment parameters according to said changes and adjusting said triglyceride levels.

15. A method according to claim 1, further comprising:
measuring a glycemic level in said diabetic patient;
selecting said patient for treatment according to said glycemic level being above a glycemic threshold;
applying said treatment to said selected patient to reduce said glycemic level.

16. A method according to claim 15, wherein said glycemic level comprises an HbA1c level>=8%.

17. A method according to claim 1, further comprising selecting said patient for treatment according to said patient taking at least one oral diabetes medication.

18. A method according to claim 17, wherein said at least one oral diabetes medication comprises one or more of; insulin, GLP-1 receptor agonist therapy, oral antidiabetic agent.

19. A method according to claim 1, further comprising:
measuring a weight of said diabetic patient;
selecting said patient for treatment according to said weight level being above a weight threshold; and
applying said treatment to said selected patient to reduce said weight.

20. A method according to claim 19, wherein said weight threshold comprises a BMI>=25.0 kg/m$^2$.

21. A method according to claim 20, wherein said reduce weight comprises reduce weight by at least 5 kg after 6 months of said treatment.

22. A method according to claim 1, further comprising:
calculating a HOMA-IR of said diabetic patient to establish a baseline;
applying said treatment to said patient to reduce said HOMA-IR relative to said baseline.

23. A method according to claim 22, wherein applying comprises applying said treatment to reduce said HOMA-IR by at least about 2.0 points after about 6 months of said treatment.

24. A method according to claim 1, wherein said applying comprises applying to extend life of beta cells.

25. A method according to claim 1, further comprising:
measuring a blood pressure of said diabetic patient;
selecting said patient for treatment according to said blood pressure being above at least one of a systolic and a diastolic threshold; and
applying said treatment to said selected patient to reduce said blood pressure.

26. A method according to claim 25, wherein said systolic threshold comprises 130 mmHg and said diastolic threshold comprises 80 mmHg.

27. A method according to claim 1, further comprising:
measuring an insulin/glucose ratio of said diabetic patient to establish a baseline;
applying said treatment to said selected patient to increase said insulin/glucose ratio relative to said baseline.

28. A method according to claim 1, wherein said applying comprises applying said treatment to reduce at least one of HbA1c level, HOMA-IR level, blood pressure, and patient's weight.

29. A method according to claim 1, wherein said applying comprises applying said treatment to increase an insulin to glucose ratio.

30. A method of treating at least one of weight loss and hypertension comprising:
measuring a triglyceride level in an obese patient and/or patient with hypertension;
selecting said patient for treatment according to said triglyceride level being below a triglyceride threshold; and
applying said treatment to said selected patient to reduce weight by at least about 5.0 kg after about 6.0 months of said treatment and/or applying said treatment to said selected patient to reduce at least one of systolic and diastolic blood pressure, said treatment comprising at least one of intra-abdominal and gastric electrical stimulation.

31. A method according to claim 30, wherein said triglyceride level<=150 mg/dl.

32. An apparatus for patient medical therapy comprising:
at least one electrode sized and shaped for contacting at least one of abdominal and gastric tissue;
a controller, said controller in electrical communication with said at least one electrode, said controller programmed to deliver electrical stimulation to said tissue; and
a memory in electrical communication with said controller, wherein a table is stored on said memory for indicating one or more treatment parameters of said electrical stimulation based on a correlation with a triglyceride level of said patient.

33. An apparatus according to claim 32, wherein said memory further comprises an indication between said triglyceride level with drug treatment parameters, and apparatus is used in combination with the administration of drugs.

34. An apparatus according to claim 32, wherein said memory is implanted.

35. An apparatus according to claim 32, wherein said memory is externally located and communicates with said controller by a programmer.

36. An apparatus according to claim 32, wherein said apparatus is packaged with instructions.

37. An apparatus according to claim 32, wherein said apparatus is used for treating a diabetic patient having an HbA1c level above a threshold.

38. An apparatus according to claim 32, wherein said table stored on said memory is used for indicating treatment parameters so that said treatment reduces an HbA1c level.

39. A method of improving insulin resistance and/or an insulin/glucose ratio in a patient comprising:
measuring a triglyceride level in said patient;

selecting said patient for treatment according to said triglyceride level being below a threshold, and according to a need to improve one or both of insulin resistance and an insulin/glucose ratio;

applying said treatment to said selected patient, said treatment comprising at least one of intra-abdominal and gastric electrical stimulation so that said insulin resistance and/or said insulin/glucose ratio is improved in said patient.

40. A method according to claim 39, wherein said threshold comprises a triglyceride level<=150 mg/dl.

41. A method of treating a diabetic patient comprising:

measuring a triglyceride level in said diabetic patient;

providing a medicament to reduce said triglyceride level in said patient during at least one of before and during said treatment;

applying said treatment to said selected patient, said treatment comprising at least one of intra-abdominal and gastric electrical stimulation, said treatment selected according to said reduced triglyceride level.

42. A method of treating a diabetic patient comprising:

modifying a treatment according to a triglyceride level of said patient, said treatment comprising at least one of intra-abdominal and gastric electrical stimulation; wherein said modifying comprises selecting said treatment according to said triglyceride level.

43. A method according to claim 42, further comprising:

modifying said triglyceride level of said patient.

* * * * *